United States Patent
Sieweke

(10) Patent No.: US 8,574,903 B2
(45) Date of Patent: Nov. 5, 2013

(54) METHOD FOR EXPANDING MONOCYTES

(75) Inventor: Michael Sieweke, Ceyreste (FR)

(73) Assignee: Inserm (Institut Natuonal de la Santa et de la Recherche Medicale), Paris (FR)

(*) Notice: Subject to any disclaimer, the term of this patent is extended or adjusted under 35 U.S.C. 154(b) by 8 days.

(21) Appl. No.: 13/359,320

(22) Filed: Jan. 26, 2012

(65) Prior Publication Data

US 2012/0122207 A1 May 17, 2012

Related U.S. Application Data

(62) Division of application No. 12/522,302, filed as application No. PCT/EP2008/050221 on Jan. 10, 2008.

(30) Foreign Application Priority Data

Jan. 11, 2007 (EP) .................................. 07300717

(51) Int. Cl.
*C12N 5/00* (2006.01)
*C12N 5/02* (2006.01)

(52) U.S. Cl.
USPC ........................................................ 435/375

(58) Field of Classification Search
USPC ........................................................ 435/375
See application file for complete search history.

(56) References Cited

U.S. PATENT DOCUMENTS

| | | | |
|---|---|---|---|
| 5,958,671 | A | 9/1999 | Glimcher et al. |
| 7,019,028 | B2 | 3/2006 | Eder et al. |
| 7,524,492 | B2 | 4/2009 | Sharma |
| 2005/0004034 | A1 | 1/2005 | Glimcher et al. |

FOREIGN PATENT DOCUMENTS

| | | |
|---|---|---|
| WO | 02/06308 | 1/2002 |
| WO | 2005/005620 | 1/2005 |

OTHER PUBLICATIONS

Aziz et al., "Development of macrophages with altered actin organization in the absence of MafB," Mol. Cell. Biol., 26 (18):6808-6818 (2006) XP002428973.

Cao et al., "The protooncogene c-Maf is an essential transcription factor for IL-10 gene expression in macrophages," J. Immunol., 174(6):3484-3492 (2005) XP002428972.
Hamada et al., "mafB deficient mouse results in impaired macrophage differentiation," Blood, 106(11):626A-627A (2005) XP009082036.
Hegde et al., "c-MAF is required for normal developmental hematopoiesis," Blood, 96(11 Pt 1):673a (2000) XP002428971.
International Search Report in PCT/EP08/50221, dated Apr. 21, 2008.
Appeal Brief in U.S. Appl. No. 12/522,302 dated Oct. 11, 2011.
Appeal Docketing Notice in U.S. Appl. No. 12/522,302 dated Feb. 1, 2012.
Examiner's Answer to Appeal Brief in U.S. Appl. No. 12/522,302 dated Nov. 16, 2011.
Final Rejection in U.S. Appl. No. 12/522,302 dated Feb. 4, 2011.
Non-Final Rejection in U.S. Appl. No. 12/522,302 dated Sep. 2, 2010.
Notice of Reply Brief entered and considered in U.S. Appl. No. 12/522,302 dated Jan. 25, 2012.
Pre-Brief Appeal Conference decision in U.S. Appl. No. 12/522,302 dated Jul. 11, 2011.
Pre-Brief Conference request and Notice of Appeal Filed in U.S. Appl. No. 12/522,302 dated Jun. 6, 2011.
Preliminary Amendment in U.S. Appl. No. 12/522,302 dated Jul. 7, 2009.
Request for Oral Hearing and Reply Brief in U.S. Appl. No. 12/522,302 dated Jan. 17, 2012.
Requirement for Restriction/Election in U.S. Appl. No. 12/522,302 dated May 19, 2010.
Response to Election/Restriction Filed in U.S. Appl. No. 12/522,302 dated Jul. 30, 2010.
Response to Restriction Requirement in U.S. Appl. No. 12/522,302 dated Jun. 21, 2010.
Takahashi, Satoru (principal investigator) Regulation mechanism of hematopoietic cell differentiation by transcription factors Scientific Research Grant No. 14370040, Mar. 2004, 1 page english translation.

*Primary Examiner* — Brian Whiteman
(74) *Attorney, Agent, or Firm* — McAndrews, Held & Malloy Ltd.

(57) ABSTRACT

The invention relates to an ex vivo method for expanding monocytes, macrophages or dendritic cells, which method comprises inhibiting the expression or the activity of MafB and c-Maf in monocytes, macrophages or dendritic cells; and expanding the cells in the presence of at least one cytokine or an agonist of cytokine receptor signaling.

8 Claims, 6 Drawing Sheets

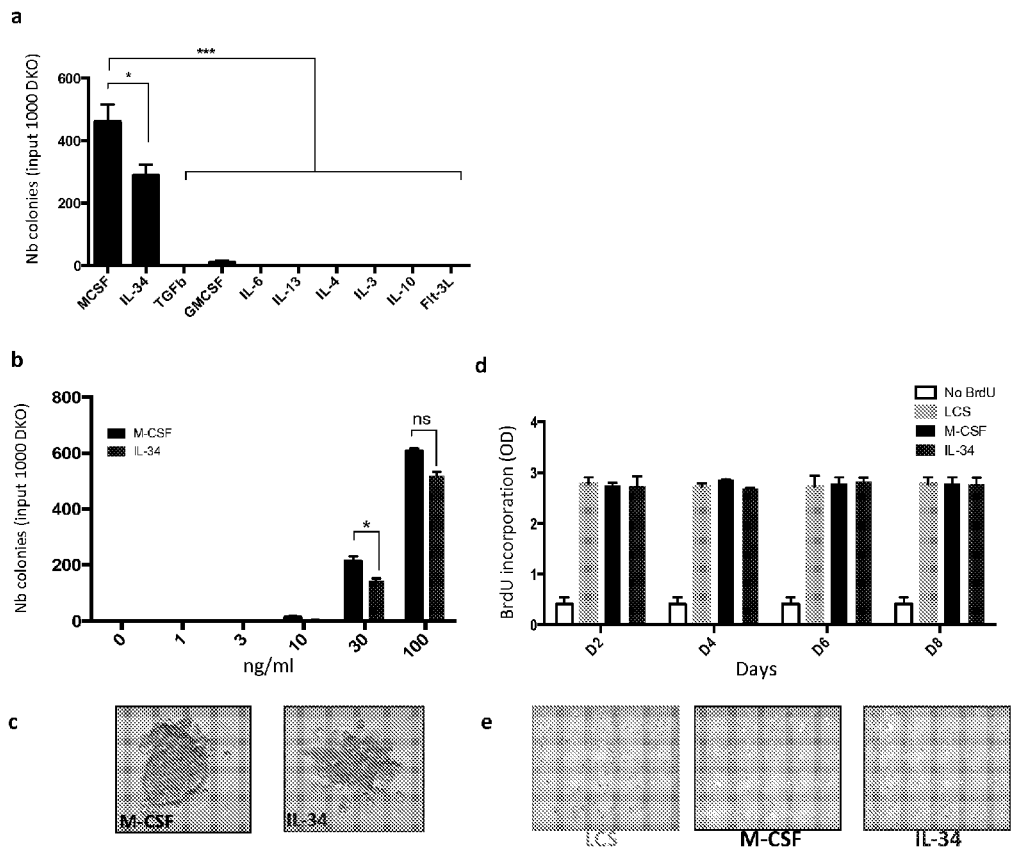

Figure 3:
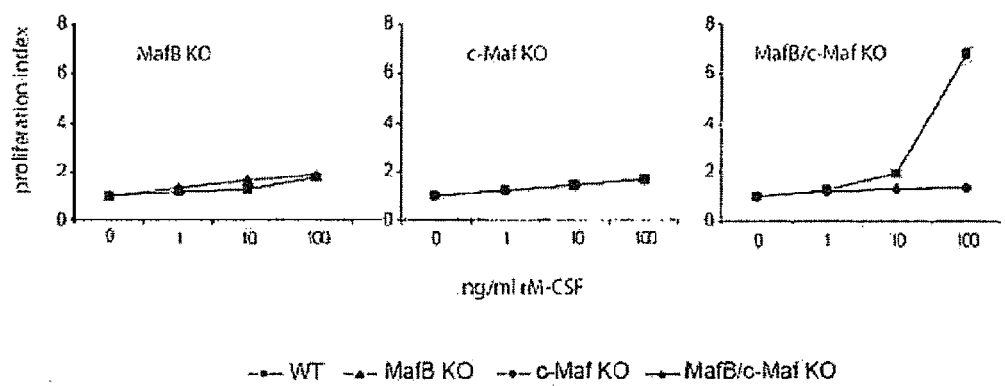

Figure 1. IL-34 sustains proliferation of M-CSF derived Maf-DKO macrophages. (a) Colony assay of M-CSF derived Maf-DKO macrophages after 14 days in single cytokine methocult medium, showing colony-forming unit numbers. (b) Colony assay of M-CSF derived macrophages upon a dose response of either M-CSF (black) or IL-34 (blue). (c) Typical morphology of macrophages colonies obtained by M-CSF (black) or IL-34 stimulation (blue). (d) in vitro proliferation assay, showing the incorporation of BrdU by macrophages stimulated with LCS (grey), M-CSF (black) or IL-34 (blue), from day 2 (D2) to day 8 (D8). (e) Typical morphology of Maf-DKO macrophages in liquide culture upon LCS (grey), M-CSF (black) or IL-34 (blue) stimulation.

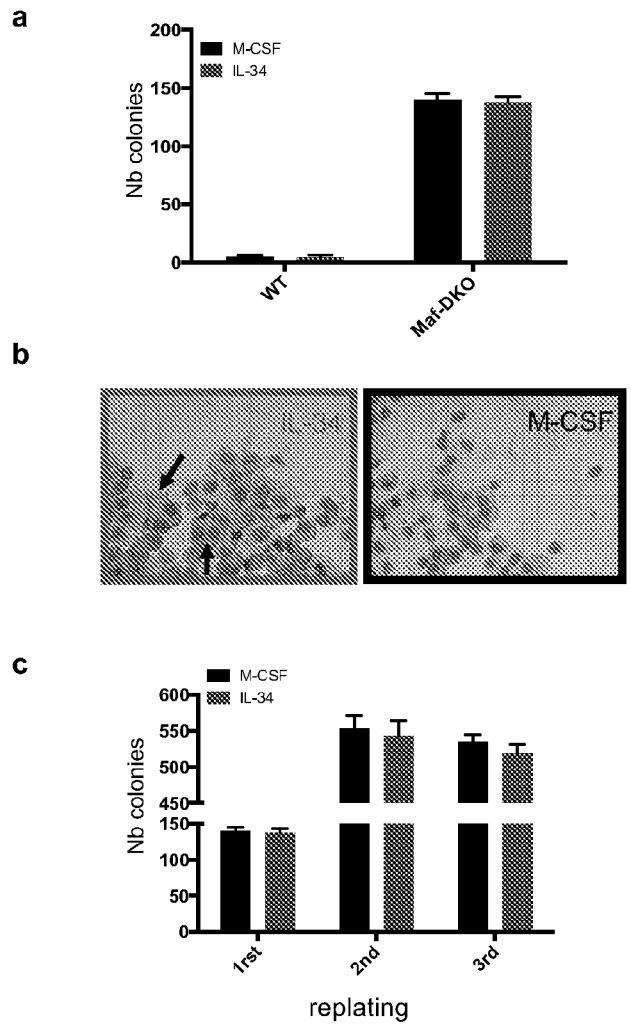

Figure 2. Maf-DKO macrophages have a colony forming potential in IL-34. (a) Colony assay of WT or Maf-DKO blood leukocytes after 14 days in M-CSF (black) or IL-34 (blue) methocult medium, showing the number of colnies. (b) Giemsa staining of M-CSF (black) or IL-34 (blue) Maf-DKO derived macrophages; arrows show cells undergoing division. (c) Serial replating in methocult of monocytes derived Maf-DKO cells washed out from M-CSF (black) or IL-34 (blue) colony assays.

METHOD FOR EXPANDING MONOCYTES

The present application is filed as a divisional application of U.S. Patent application Ser. No. 12/522,302, which was filed Jan. 10, 2008, which was filed pursuant to 35 U.S.C. 371 as a U.S. National Phase application of International Patent Application No. PCT/EP08/50221, which was filed Jan. 10, 2008, claiming the benefit of priority to European Patent Application No. 07300717.1, which was filed on Jan. 11, 2007. The entire text of the aforementioned applications is incorporated herein by reference in its entirety.

The invention relates to a method for generating, maintaining and expanding monocytes, macrophages or dendritic cells in long term culture.

BACKGROUND OF THE INVENTION

Monocytes are generated in the bone marrow (BM) to be released in the blood stream and give rise to different types of tissue-macrophages or dendritic cells after leaving the circulation. Monocytes, their progeny and immediate precursors in the bone marrow have also been named the 'mono-nuclear phagocyte system' (MPS). They are derived from granulocyte/macrophage colony forming unit (CFU-GM) progenitors in the bone marrow that gives rise to monocytic and granulocytic cells. The maturation process of the monocytic lineage in vivo passes from a monoblast stage, through the promonocyte stage to mature monocytes (Goud T J et al. 1975). IL-3, GM-CSF and macrophage colony stimulating factor (M-CSF) stimulate in vivo generation of monocytes (Metcalf D et al. 1990). In vitro, hematopoietic progenitor cells cultured with GM-CSF induce CFU-GM to differentiate towards granulocytes, while addition of FL and SCF shifts differentiation from the granulocytic to the monocytic lineage (Gabbianelli M et al. 1995; Willems R et al. 2001).

Several recent studies indicate that although specific surface marker expression may vary in detail between species, the general differentiation pathways of monocytes and their progeny appear to be largely conserved between mice and humans (Gordon S et al. 2005). With the higher accessibility to experimentation a more detailed differentiation pathway could be worked out in the animal model. Mouse monocytes originate from hematopoietic stem cells (HSC) in the bone marrow via successive commitment steps and several intermediate prognitor stages with increasingly restricted differentiation potential (Shizuru J A et al. 2005; Kondo M et al. 2000). This differentiation series is believed to pass through the common myeloid progenitor (CMP), which can give rise to all myeloid cells, to the granulocyte-macrophage progenitor (GMP), which gives rise to monocytic and granulocytic cells and may be identical or very similar to CFU-GM progenitors. Yet a more immediate monocytic progenitor in the bone marrow appears to be the macrophage/dendritic cell progenitor (MDP) that can give rise to macrophages and dendritic cells, likely via a monocyte intermediate stage (Fogg et al 2006).

Newly formed monocytes leave the BM within 24 hours and migrate to the peripheral blood. Circulating monocytes can adhere to endothelial cells of the capillary vessels and are able to migrate into various tissues (van Furth R. et al. 1992), where they can differentiate into macrophages or dendritic cells. These adherence and migration involve surface proteins, lymphocyte-function associated antigen-1 (LFA-1), CD11 and antigen-4 (VLA-4), belonging to the integrin superfamily of adhesion molecules (Kishimoto T K et al. 1989). These integrins interact with selectins on endothelial cells. Monocyte derived macrophages can show a high degree of heterogeneity that reflects a morphological and functional specification adopted in the infiltrated tissue. According to their anatomical localization they may also have distinct names (e.g. microglia in the central nervous system and Kupffer cells in the liver).

Although it remains controversial, whether some resident macrophage populations may be capable of proliferating in situ under certain conditions, the majority of macrophages appear to have no or a very limited proliferation capacity (Gordon 8, et al., 2005). The renewal of tissue macrophage populations therefore depends on the influx of monocytes and their local differentiation (Crofton R W et al. 1978; Blusse van Oud Alblas A et al; 1981). Although such tissue infiltrating monocytes can have a very limited proliferation ability, monocytes circulating in the blood do not cycle and rapidly differentiate into macrophages rather than expand, when stimulated with M-CSF ex vivo.

Monocyte recruitment to tissues differs under homeostatic and inflammatory conditions and appears to involve two distinct monocyte populations that have been identified in humans and mammalian animal models (Gordon 8, et al. 2005). During inflammation monocytopoiesis increases (Shum D T et al 1982; van Waarde D et al. 1977) resulting in elevated monocyte numbers. Furthermore, inflammatory mediators, IL-1, IL-4. IFN-γ and TNF-α upregulate expression of selectins on endothelial cells, promoting migration of monocytes into tissues. The same cytokines modulate expression of integrin adhesion molecules on monocytes (Pober J S et al. and 1990). At the site of inflammation monocytes are involved in the phagocytosis of opsonized microorganisms or immune complexes via surface γreceptors (CD64, CD32) and complement receptors (CD11b. CD11c). The microorganisms are synergistically killed by reactive oxygen and nitrogen metabolites and through several hydrolytic enzymes (acid phosphatase, esterase, lysozyme and galactosidase) (Kuijpers T. 1989; Hibbs J B et al. 1987). Importantly, monocyte derived macrophages and dendritic cells stimulate T cells by antigen presentation and thus, are involved in the recognition and activation phases of adaptive immune responses (Nathan C F. 1987). Monocytes also secrete a large number of bioactive products which play an important role in inflammatory, proliferative and immune responses, including growth factors (GM-CSF, G-CSF, M-CSF, IL-1) and antiproliferating factors (IFNs, TNF).

Lipopolysaccharide (LPS) or endotoxin is a predominant integral structural component of the outer membrane of Gram-negative bacteria and one of the most potent microbial initiators of inflammation. LPS binds to the CD14 glycoprotein that is expressed on the surface of monocytes and stimulates the toll receptor pathway via activation of TLR4. Other PAMPs (pathogen associated molecular patterns) can also initiate inflammatory responses via other TLR receptors. The binding of LPS or other PAMPS induces production of TNF-α, IL-1, -6, -8 and -10 (Wright S D. Et al; 1990; Dobrovolskaia M A et al. 2002; Foey A D. et al. 2000).

Other than LPS or other PAMPs, one of the most efficient stimuli for cytokine production in vitro is the direct cell-cell contact of monocytes with activated lymphocytes (Way E. et al. 1992; Parry S L. Et al. 1997), via CD40 ligand (CD40L) (Wagner D H. Et at 1997; Shu U. et al. 1995; Alderson M R. et al. 1993). This interaction may also be important in the immune surveillance of tumors. Thus the incubation of monocytes with CD40L-transfected cells results in tumoricidal activity against a human melanoma cell line. Furthermore functional interactions have also been described between monocytes and NK cells, a cell type with significant anti-tumor activity. Both direct cell-cell contact (Miller J S. Et al. 1992). and release of soluble factors such as IL-12, TNF-α, IL-15 or IL-1β by activated monocytes induce proliferation, production of IFN-γ (Carson W E et al. 1995; Tripp C S. et al. 1993) and the cytotoxic potential of cocultured NK cells in a time dependent manner (Chang Z L, et al. 1990; Bloom E T. et al. 1986).

Finally macrophages are also critically involved in wound healing and tissue repair, where they assume trophic functions by removing debris and orchestrating the recruitment and activity of other cell types participating in tissue remodelling (Gordon S of at 2003)

Dendritic cells (DCs) are components of the innate immune system. They are antigen presenting cells with the unique ability to induce a primary immune response (Banchereu et al. 2000). They can be derived from circulating monocytes or circulating DC progenitors in the blood and non-lymphoid peripheral tissues, where they can become resident cells (Banchereau J. et al. 1998, 2000) (Geissmann, 2007) (Wu and Liu, 2007). Immature DCs (iDCs) recognize pathogens through cell surface receptors, including Toll-like receptors (Reis a Sousa C. 2001). After uptake of antigen DCs mature and migrate to lymph nodes. Mature DCs (mDCs) are efficient antigen presenting cells (APCs) which mediate T cell priming (Banchereau J. et al. 1998, 2000). Furthermore a predominant role of DCs has been described in NK cell activation in mice and humans. Both immature and bacterially activated human monocyte-derived DCs have been shown to induce cytokine secretion and cytotoxicity by NK cells (Ferlazzo G. et al. 2002; Fernandez N C, et al. 1999).

The in vitro differentiation of murine macrophages from bone marrow in the presence of M-CSF was described by Stanley et al. (1978, 1986). Whereas progenitor cells will initially proliferate in response to M-CSF, they eventually differentiate to mature macrophages and terminally withdraw from the cell cycle (Pixley and Stanley, 2004). Thus even though the macrophages generated this way will survive for a limited time, they are not homogeneous and cannot be further expanded in culture. Similarly human monocytes do not proliferate in response to M-CSF but initiate morphological changes indicative of macrophage differentiation (Becker et al., 1987). Although a significant number of monocytes can be obtained from a patient by leukapheresis and elutriation (Stevenson et al., 1983), these cells will further differentiate to macrophages in a few days without proliferating and cannot be maintained in culture.

Now, the present invention provides a new in vitro method for generating, maintaining and expanding monocytes and macrophages in long term culture.

The inventors have indeed demonstrated that it is possible to expand and maintain monocytes and macrophages in culture for weeks or months, by inactivating the expression of MafB and c-Maf in said cells. Not only in vitro generated macrophages but also mature bone marrow MafB and c-Maf deficient macrophages and blood monocytes continue to proliferate in culture.

Methods of the invention may thus be useful for therapeutic approaches requiring amplification of monocytes and monocyte derived cells, as well as for screening for drugs targeting monocyte, monocyte derived macrophages (including osteoclasts) and dendritic cells or for testing the response to specific drugs in a patient specific way, or for studying the molecular basis of monocyte or monocyte derived cell dependent diseases by culturing and expanding monocyte or monocyte derived cells of afflicted patients.

SUMMARY OF THE INVENTION

The present invention provides an ex vivo method for expanding monocytes, macrophages or dendritic cells, which method comprises inhibiting the expression or the activity of MafB and c-Maf in monocytes, macrophages or dendrite cells; and expanding the cells in the presence of at least one cytokine, e.g. M-CSF.

An object the invention is also a monocyte, macrophage or dendritic cell obtainable by the above method.

Another object of the invention is a monocyte, macrophage or dendritic cell, which does not express MafB and c-Maf or in which the expression or activity of MafB and c-Maf is abolished or inhibited.

Such monocyte, macrophages or dendritic cells are useful in a pharmaceutical composition, where they are in combination with a pharmaceutically acceptable carrier.

A particular object of the invention is a pharmaceutical composition which comprises such dendrite cell, loaded with an antigenic molecule, for use as a vaccine.

The invention further provides the use of a monocyte, macrophage or dendritic cell as defined above, for the screening of drugs.

The invention further provides a method for generating and expanding murine monocytes, which method comprises the steps consisting of:

i) isolating monocytes derived from a mouse which does not express MafB and c-Maf and ii) culturing said monocytes in the presence of M-CSF.

DETAILED DESCRIPTION

Definitions

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. A "promoter" or "promoter sequence" is a DNA regulatory region capable of binding RNA polymerase in a cell and initiating transcription of a downstream (3' direction) coding sequence. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

As used herein, references to specific proteins (e.g., MafB or c-Maf) can include a polypeptide having a native amino acid sequence, as well as variants and modified forms regardless of their origin or mode of preparation. A protein that has a native amino acid sequence is a protein having the same amino acid sequence as obtained from nature (e.g., a naturally occurring MafB or c-Maf). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including postranslational modifications. A native sequence protein includes proteins following post-translational modifications such as glycosylation, or phosphorylation, ubiquitination, sumoylation or other modifications of some amino acid residues.

The terms "mutant" and "mutation" mean any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Mutations include deletion, insertion or substitution of one or more nucleotides. The mutation may occur in the coding region of a gene (i.e. in exons), in introns, or in the regulatory regions (e.g. enhancers, response elements, suppressors, signal sequences, polyadenylation sequences, promoters) of the gene. Generally a mutation is identified in a subject by comparing the sequence of a nucleic acid or polypeptide expressed by said subject with the corresponding nucleic acid or polypeptide expressed in a control population. Where the mutation is within the gene coding sequence, the mutation may be a "missense" mutation, where it replaces one amino acid with another in the gene product, or a "non sense" mutation, where it replaces an amino acid codon with a stop codon. A mutation may also occur in a splicing site where/it creates or destroys signals for exon-intron splicing and thereby lead to a gene product of altered structure. A mutation in the genetic material may also be "silent", i.e. the mutation does not result in an alteration of the amino acid sequence of the expression product.

Variants refer to proteins that are functional equivalents to a native sequence protein that have similar amino acid sequences and retain, to some extent, one or more activities of the native protein. Variants also include fragments that retain activity. Variants also include proteins that are substantially identical (e.g., that have 80, 85, 90, 95, 97, 98, 99%, sequence identity) to a native sequence. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein (see, e.g., Creighton (1984) Proteins, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed. The variations can be made using methods known in the art such as site-directed mutagenesis (Carter, et al. (1985); Zoller et al. (1982) Nucl. Acids Res. 10:6487), cassette mutagenesis (Wells et al. (1985) Gene 34:315), restriction selection mutagenesis (Wells, et al. (1986) Philos, Trans. R. Soc. London SerA 317:415), and PCR mutagenesis (Sambrook et al., 2001).

Two amino acid sequences are "substantially homologous" or "substantially similar" when greater than 80% preferably greater than 85%, preferably greater than 90% of the amino acids are identical, or greater than about 90%, preferably greater than 95% are similar (functionally identical). Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyrne, structural RNA or any other type of RNA) or a protein produced by translation of a mRNA. Gene products also include messenger RNAs which are modified, by processes such as capping, polyadenylation, methylation, and editing, and proteins (e.g., MafB or c-Maf) modified by, for example, methylation, acetylation, phosphorylation, ubiquitination, SUMOylation, ADP-ribosylation, myristilation, and glycosylation.

An "inhibitor of expression" refers to a natural or synthetic compound that reduces or suppresses the expression of a gene.

An "inhibitor of activity" has its general meaning in the art, and refers to a compound (natural or not) which has the capability of reducing or suppressing the activity of a protein.

The term "c-Maf" denotes the c-Maf proto-onocogene, which is identical in sequence to the v-Maf oncogene of AS42 virus and can transform chicken embryo fibroblasts (Nishizawa et al. PNAS 1989). C-Maf and other Maf family members form homodimers and heterodimers with each other and with Fos and Jun, consistent with the known ability of the AP-1 proteins to pair with each other (Kerppola, T. K. and Curran, T. (1994) Oncogene 9:675-684; Kataoka, K. et al. (1994) Mot, Cell. Biol. 14; 700-712). The DNA target sequence to which c-Maf homodimers bind, termed the c-Maf response element (MARE), is a 13 or 14 bp element which contains a core TRE (T-MARE) or CRE (C-MARE) palindrome respectively, but c-Maf may also bind to DNA sequences diverging from these consensus sites including composite AP-1/MARE sites and MARE half sites with 5' AT rich extensions (Yoshida et al. NAR2005). c-Maf has been shown to stimulate transcription from several promoters, including the Purkinje neuron-specific promoter L7 (Kurscher, C. and Morgan, J. I. (1994) Mol. Cell. Biol. 15:246-254), $\alpha,\beta\gamma$-Crystallin (Ring at al. Development, 2000, Kim et al. PNAS 1999; Kawauchi et al. JBC1999, Yang et al., JMB 2005), insulin (Matsuoka, et al. MCB, 2003) and p53 (Hale et al., JBC 2000) promoters as well as to repress the transcription of other promoters such as the early myeloid promoter AND/CD13 (Hedge et al., 1998). c-Maf has also been shown to induce the differentiation of T helper 2 (Th2) cells (Ho et al., 1996) due to its ability to activate the tissue specific transcription of the interleukin-4 (IL-4) (Kim et al. 1999). Furthermore the over-expression of c-Maf in myeloid cell lines induces macrophage differentiation (Hegde et al., 1999). The nucleotide sequence of the mouse c-maf proto-oncogene, and predicted amino acid sequence for the mouse c-Maf protein, have been described (Kurscher, C. and Morgan, J. I. (1995) Mol, Cell. Biol. 15:246-254; and Genbank Accession number S74567). The nucleotide sequence of the chicken c-maf proto-oncogene, and predicted amino acid sequence for the chicken c-Maf protein, also have been described (Kataoka et al. 1994, Genbank Accession number D28596). The nucleotide sequence of the human c-maf proto-oncogene, and predicted amino acid sequence for the human c-Maf protein, also have been described (U.S. Pat. No. 6,274, 338 and Genbank Accession number BD106780)

The term "MafB" denotes the MafB transcription factor. This gene is expressed in a variety of cell types (including lens epithelial, pancreas endocrine, chondrocyte, neuronal and hematopoietic cells) and encodes a protein of 311 amino acids containing a typical bZip motif in its carboxy-terminal region. In the bZip domain. MafB shares extensive homology not only with v/c-Maf but also with other Maf-related proteins. MafB can form a homodimer through its leucine repeat structure and specifically binds Maf-recognition elements (MAREs) palindromes, composite AP-1/MARE sites or MARE halfsites with AT rich 5' extensions (Yoshida, et al. 2005). In addition, MafB can form heterodimers with c-/v-Maf or Fos through its zipper structure but not with Jun or other Mai family members (Kataoka et al., 1994). MafB is also known under the name kreisler, kr or Krm1 (for 'Kreisler Maf leucine Zipper 1'), because an x-ray induced chromosomic micro-inversion in kreisler mutant mice causes the tissue specific loss of MafB expression in the developing hindbrain that is responsible for the kreisler phenotype (Cordes et al., 1994) (Eichmann et al., 1997). In the hematopoietic system MafB is expressed selectively in the myeloid lineage and is up-regulated successively during myeloid differentiation from multipotent progenitors to macrophages. Indeed, this induction reflects an important role of MafB in monocytic differentiation. Thus the overexpression of MafB in transformed chicken myeloblasts (Kelly et al., 2000, Bakri et al. 2005) and in human hematopoetic progenitors (Gemelli et al., 2006) inhibits progenitor proliferation (Tillmanns et al., 2007) and stimulates the rapid formation of macrophages (Kelly et al., 2000, Bakri et al. 2005, Gemelli et al., 2006), whereas a dominant negative version of MafB inhibits this process (Kelly et al., 2000), indicating that MafB induction is a specific and important determinant of the monocytic program in hematopoietic cells. The nucleotide sequence of the chicken (Kataoka, K. et al. 1994), mouse (Cordes et al. 1994) and human (Wang et al. 1999) MafB gene, and predicted amino acid sequences for the MafB proteins, also have been described (GenBank accession numbers NM_001030852 (*gallus gallus*), NM_010658 (*mus musculus*), NM_005461 (*homo sapiens*) D28600).

A "monocyte cell" is a large mononuclear phagocyte of the peripheral blood. Monocytes vary considerably, ranging in size from 10 to 30 μm in diameter. The nucleus to cytoplasm ratio ranges from 2:1 to 1:1. The nucleus is often band shaped (horseshoe), or reniform (kidney-shaped). It may fold over on top of itself, thus showing brainlike convolutions. No nucleoli are visible. The chromatin pattern is fine, and arranged in skein-like strands. The cytoplasm is abundant and appears blue gray with many fine azurophilic granules, giving a ground glass appearance in Giemsa staining. Vacuoles may be present. More preferably, the expression of specific surface antigens is used to determine whether a cell is a monocyte cell. The main phenotypic markers of human monocyte cells include CD11b, CD11c, CD33 and CD115. Generally, human monocyte cells express CD9, CD11b, CD11c, CDw12, CD13, CD15, CDw17, CD31, CD32, CD33, CD35, CD36, CD38, CD43, CD49b, CD49e, CD49f, CD63, CD64, CD65s, CD68, CD84, CD85, CD86, CD87, CD89, CD91, CDw92, CD93, CD98, CD101, CD102, CD111, CD112, CD115, CD116, CD119, CDw121b, CDw123, CD127, CDw128, CDw131, CD147, CD155, CD156a, CD157, CD162, CD163, CD164, CD168, CD171, CD172a, CD180, CD206, CD131a1, CD213a2, CDw210, CD226, CD281, CD282, CD284, CD286 and optionally CD4, CD14, CD16, CD40, CD45RO, CD45RA, CD45RB, CD62L, CD74, CD142 and CD170, CD181, CD182, CD184, CD191, CD192, CD194, CD195, CD197, CX3CR1. The main phenotypic markers of mouse monocyte cells include CD11b+, CD115, F4/80+. Generally mouse monocyte cells express CD11a, CD11b, CD16, CD18, CD29, CD31, CD32, CD44, CD45, CD49d, CD115, CD116, Cdw131, CD281, CD282, CD284, CD286, F4/80, and optionally CD49b, CD62L, CCR2, CX3CR1, and Ly6C. Upon contact with sensitive target cells, monocyte cells also produce a number of cytokines, including IFNs, TNFs, GM-CSF, G-CSF, M-CSF, and IL-1.

A "macrophage cell" is a cell exhibiting properties of phagocytosis. The morphology of macrophages varies among different tissues and between normal and pathologic states, and not all macrophages can be identified by morphology alone. However, most macrophages are large cells with a round or indented nucleus, a well-developed Golgi apparatus, abundant endocytotic vacuoles, lysosomes, and phagolysosomes, and a plasma membrane covered with ruffles or microvilli. The key functions of macrophages in innate and adaptive immunity are the phagocytosis and subsequent degradation of senescent or apoptotic cells, microbes and neoplastic cells, the secretion of cytokines, chemokines and other soluble mediators, and the presentation of foreign antigens (peptides) on their surface to T lymphocytes. Macrophages are derived from common myeloid progenitor cells and granulocyte-monocyte progenitor cells in the bone marrow of mammalian organisms, which ultimately develop through further progenitor stages into monocytes that then enter the peripheral bloodstream. Unlike neutrophils, with their multi-lobed nuclei, monocytes have kidney-shaped nuclei and assume a large cell body during further differentiation and activation. Throughout life, some monocytes adhere to and migrate through the endothelium of the capillaries into all organs, where they differentiate into resident tissue macrophages or dendritic cells (see below). Besides a monocyte origin a limited self renewal capacity has also been reported for some subpopulations of tissue macrophages. Lymphatic tissues, such as the lymph nodes and the spleen, are particularly rich in macrophages. In some organs the macrophages carry special names, as summarized in Table 1.

TABLE 1

Examples of tissue macrophages

| Organ | Macrophage population |
|---|---|
| Bone | Osteoclasts |
| Central nervous system | Microglia |
| Connective tissue | Histiocytes |
| Chorion villi of the placenta | Hofbauer cells |
| Kidney | Mesangial cells |
| Liver | Kupffer cells |
| Peritoneal cavity | Peritoneal macrophages |
| Pulmonary airways | Alveolar macrophages |
| Skin | Epidermal and dermal macrophages |
| Spleen | Marginal zone macrophages, Metallophilic macrophages, Red pulp macrophages, White pulp macrophages |

In the context of the invention, the macrophage is selected from the group consisting of microglia, histiocytes, Hofbauer cells, mesangial cells, Kupffer cells, peritoneal macrophages, alveolar macrophage, epidermal or dermal macrophages, marginal zone macrophages, metallophilic macrophages. Red pulp macrophages, white pulp macrophages and osteoclasts. Bone marrow or fetal liver derived macrophages are particularly useful.

Osteoclasts are a specialized cell type of the mononuclear phagocyte system that is specific to bone and serves an important homeostatic and remodelling function in this tissue by degrading its mineralized components. In culture, osteoclasts can be derived from CFU-GM progenitors of the bone marrow and from blood monocytes by culture in M-CSF and RANKL. The importance of these cytokines for osteoclast development is underscored by osteoclast deficiency and development of osteopetrosis in mice with deletions of either of these two factors. Although it has not been shown formally in vivo, it is widely assumed that circulating blood monocytes serve as osteoclast precursors. Aberrant osteoclast development and/or activity play a prominent role in debilitating human pathologies of high prevalence and with limited treatment options, such as osteoporosis, osteopetrosis and osteoarthritis (Boyle W J et al. 2003; Teitelbaum S L et al. 2003).

Macrophages are an important source of cytokines. Functionally, the numerous products can be placed into five major groups: (1) cytokines that mediate a proinflammatory response, i.e. help to recruit further inflammatory cells (e.g. IL-1, IL-6, TNFs, CC and CXC chemokines, such as IL-8 and monocyte-chemotactic protein 1); (2) cytokines that mediate T cell and natural killer (NK) cell activation (e.g. IL-1, IL-12, IL-18); (3) cytokines that exert a feedback effect on the macrophage itself (e.g. IL-1, TNFs, IL-12, IL-18, M-CSF, IFNα/β, IFNγ); (4) cytokines that downregulate the macrophage and/or help to terminate the inflammation (e.g. IL-10, TGFβs), (5) cytokines important for wound healing (e.g. EGF, PDGF, bFGF, TGFβ). The production of cytokines by macrophages can be triggered by microbial products such as LPS, by interaction with type 1 T-helper cells, or by soluble factors including prostaglandins, leukotrienes and, most importantly, other cytokines (e.g. IFNγ). Generally, human macrophages express CD11c, CD11b, CD18, CD26, CD31, CD32, CD36, CD45RO, CD45RB, CD63, CD68, CD71, CD74, CD87, CD88, CD101, CD119, CD121b, CD155, CD156a, CD204, CD206 CDw210, CD281, CD282, CD284, CD286 and in a subset manner CD14, CD16, CD163, CD169 CD70 and MARCO. Mouse monocytes further express F4180 and do not express CD11c. Activated macrophages further express CD23, CD25, CD69 and CD105.

A "dendritic cell" (DC) is an antigen presenting cell existing in vivo, in vitro, ex vivo, or in a host or subject, or which can be derived from a hematopoietic stem cell, a hematopoietic progenitor or a monocyte. Dendritic cells and their precursors can be isolated from a variety of lymphoid organs, e.g., spleen, lymph nodes, as well as from bone marrow and peripheral blood. The DC has a characteristic morphology with thin sheets (lamellipodia) extending in multiple directions away from the dendritic cell body. DCs express constitutively both MHC class I and class II molecules, which present peptide antigens to CD8+ and CD4+ T cells respectively. In addition, human skin and mucosal DCs also express the CD1 gene family, MHC class I-related molecules that present microbial lipid or glycolipid antigens. The DC membrane is also rich in molecules that allow adhesion of T cells (e.g. intercellular adhesion molecule 1 or CD54) or that co-stimulate T-cell activation such as B7-1 and B7-2 (also known as CD80 and CD86 respectively). Generally, DCG express CD85, CD180, CD187 CD205 CD281, CD282, CD284, CD286 and in a subset manner CD206, CD207, CD208 and CD209.

By "purified" and "isolated" it is meant, when referring to a polypeptide or a nucleotide sequence, that the indicated molecule is present in the substantial absence of other biological macromolecules. When referring to a cell or a population of cells, the term means that said cell or said population of cells is present in the substantial absence of other cells or population of cells. The term "purified" as used herein preferably means at least 75% by weight or number, more preferably at least 85% by weight or number, still preferably at least 95% by weight or number, and most preferably at least 98% by weight or number, of biological macromolecules or cells of the same type are present. An "isolated" nucleic acid molecule, which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a vertebrate, preferably a mammal, such as a rodent, e.g. a mouse; a feline, a canine, and a primate. Most preferably a subject according to the invention is a human. Most preferably the monocytes, macrophages, or dendritic cells expanded according to the method of the invention are thus human cells.

In the context of the invention, the term "treating" or "treatment", as used herein, means reversing, alleviating, inhibiting the progress of, or preventing the disease or condition to which such term applies, or one or more symptoms of such disease or condition.

Methods for Generating and Expanding Monocytes in Long Term Culture

The inventors have demonstrated that it is possible to generate, maintain and expand monocytes in culture for several months, by inactivating in said cells the expression of MafB and c-Maf.

The invention thus provides an ex vivo method for expanding monocytes, macrophages or dendritic cells, which method comprises inhibiting the expression or the activity of MafB and c-Maf in monocytes, macrophages or dendritic cells; and expanding the cells in the presence of at least one cytokine or an agonist of cytokine receptor signaling.

The monocytes, macrophages or dendritic cells that serve as starting material may be isolated according to any technique known in the art.

Methods for isolating starting monocytes are well known in the art and include those described by Fluks A J. (1981); Hardin J A. et al. (1981); Harwood R. (1974); Elias J A et al. (1985); Brandslund I et al. (1982); Pertoft H et al. (1980); Nathanson S D et al. (1977); Loos H et al. (1976), What S M, et al. (1984). Macrophages and dendritic cells may be derived in vitro from monocytes by differentiation (Stanley et al., 1978, 1986; Gieseler R et al. 1998, Zhou et al. 1996; Cahpuis at 1997, Brossart et al. 1998, Palucka at 1998). In mice macrophages and DC may be obtained from spleen suspensions (Fukao, T., and Koyasu, S., 2000; Fukao, T., Matsuda, S., and Koyasu, S. 2000), from the peritoneal cavity (Mishell, B. B. and Shiigi, S. M. (1980) or most commonly from different fetal liver or bone marrow progenitors using various cytokine cocktails (Ardavin et al., 2001)

One other standard method for isolating monocytes, macrophages or dendritic cells consists in collecting a population of cells from a subject and using differential antibody binding, wherein cells of one or more certain differentiation stages are bound by antibodies to differentiation antigens. Fluorescence activated cell sorting (FACS) may be therefore used to separate the desired cells expressing selected differentiation antigens from the population of isolated cells. In another embodiment, magnetic beads may be used to isolate monocytes, macrophages or dendritic cells from a cell population (MACS). For instance, magnetic beads labelled with monoclonal cell type specific antibodies may be used for the positive selection of human monocytes, macrophages and dendritic cells from cord blood, peripheral blood, or PBMCs, as well as pleural, peritoneal, or synovial fluids or from various tissues, such as spleen and lymph node. Other methods can include the isolation of monocytes by depletion of non-monocytes cells (negative selection). For instance non-monocytes cells may be magnetically labeled with a cocktail of monoclonal antibodies chosen antibodies directed against CD3, CD7, CD19, CD56, CD123 and CD235a. Kits for isolation of monocytes, macrophages and dendritic cells are commercially available from Miltenyi Biotec (Auburn, Calif., USA), Stem Cells Technologies (Vancouver, Canada) or Dynal Bioech (Oslo, Norway).

Methods for isolation and preparation of dendritic cells and monocytes are also described in the international patent application WO2004066942 and in U.S. Pat. No. 6,194,204.

As an alternative method, monocyte progenitor populations may be derived from bone marrow or cord blood and differentiated to monocytes ex vivo by culture in M-CSF.

As a further alternative, dendritic cells and macrophages may be derived from isolated monocytes.

For example, monocytes may be differentiated into macrophages by any technique well known in the art Differentiation of monocytes to macrophages may be induced by macrophage colony-stimulating factor (M-CSF), Recent studies have shown that optimal recombinant human M-CSF-induced differentiation involves the autocrine activity of secreted interleukin 6 (IL-6), which up-regulates the expression of functional M-CSF receptors on monocytes and enhances macrophage cytotoxicity, superoxide production, phagocytosis, chemotaxis, and secondary cytokine secretion (Akira, 1996). The interplay between IL-6 and M-CSF regulates monocyte differentiation into macrophages and inhibits DC differentiation from GM-CSF/IL-4-treated monocytes (Chomarat et al, 2000, Mitani et al., 2000).

Furthermore human monocytes may be also differentiated in vitro into macrophages by a 7 day culture in hydrophobic bags (Chokri et al., 1989). Other techniques are also described in D'Onofrio C et al. (1983) or Gersuk G, et al. (2005). Other methods include those described by Salahuddin et al. (1982) and Hashimoto et al. (1997).

Monocytes may be differentiated into dendritic cells (DCs) by any technique well known in the art. For example granulocyte-macrophage colony-stimulating factor (GM-CSF) with interleukin-4 (IL-4) differentiates monocytes into DCs. Multiple methods well known to the art have been described to differentiate human blood monocytes into dendritic cells by using GM-CSF. IL-4, and/or IFN-γ and for CD40 ligation (Gieseler R et al. 1998, Zhou et al. 1996; Cahpuis et al 1997, Brossart et al. 1998, Palucka et al 1998). LC cells, a DC subset may be derived using TGF-β in addition (Strobl et al. 1997).

Methods that allow differentiation of monocyte to osteoclasts are well known in the art. For example M-CSF and RANKL differentiate monocytes into OCs (Yasuda, H. et al. 1998; Hsu, H. et al. 1999).

Differentiation of the monocytes into macrophages, or dendritic cells may occur before inhibiting MafB and c-Maf, or after.

For instance, in a particular embodiment, the method comprises:
isolating monocytes;
inhibiting the expression or activity of MafB and c-Maf in said monocytes;
culturing the monocytes wherein the expression or activity of MafB and c-Maf has been inhibited, in conditions allowing the differentiation of the monocytes into macrophages or dendritic cells.

For such differentiation, one may employ cytokines such as M-CSF.

As absence of MafB and c-Maf extends the cell expansion phase in response to M-CSF before its effect on macrophage differentiation, termination of the expansion phase and macrophage differentiation may be initiated by terminating MafB and c-Maf inhibition using any of the transient inhibition methods described below. Alternatively M-CSF concentrations may be reduced in the medium and supplemented directly with IL-6.

Inhibition of the expression or the activity of c-Maf and MafB may be achieved by any technique.

In a particular embodiment, the expression of MafB and c-Maf may be inhibited by using siRNA oligonucleotide, antisense oligonucleotide or ribozymes Anti-sense oligonucleotides, including anti-sense RNA molecules and anti-sense DNA molecules, would act to directly block the translation of c-Maf and MafB mRNA by binding thereto and thus preventing protein translation or increasing mRNA degradation, thus decreasing the level of c-Maf and MafB proteins, and thus activity, in a cell. For example, antisense oligonucleotides of at least about 15 bases and complementary to unique regions of the mRNA transcript sequence encoding for c-Maf and MafB may be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Specific methods for preparing anti-sense oligonucleotides to c-Maf are described in U.S. Pat. No. 6,274,338.

Small inhibitory RNAs (siRNAs) can also function as inhibitors of expression of c-Maf and MafB for use in the present invention. C-Maf and MafB gene expression can be reduced by contacting monocyte cell with a small double stranded RNA (dsRNA), or a vector or construct causing the production of a small double stranded RNA, such that expression of c-Maf and MafB is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). Specific methods for preparing siRNAs against c-Maf are also described in U.S. Pat. No. 6,274,338 and for MafB in (Kim et al. 2006).

Ribozymes can also function as inhibitors of expression of c-Maf and MafB for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of c-Maf and MafB mRNA sequences are thereby useful within the scope of the present invention. Specific ribozyme cleavage sites within any potential RNA target are initially identified by scanning the target molecule for ribozyme cleavage sites, which typically include the following sequences, GUA, GuU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Antisense oligonucleotides, siRNA oligonucleotides and ribozymes useful as inhibitors of expression of c-Maf and MafB can be prepared by known methods. These include techniques for chemical synthesis such as, e.g., by solid phase phosphoramadite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNA oligonucleotides and ribozymes of the invention may be delivered alone or in association with a vector. In its broadest sense, a "vector" is any vehicle capable of facilitating the transfer of the antisense oligonucleotide, siRNA oligonucleotide or ribozyme nucleic acid to monocytes. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA oligonucleotide or ribozyme nucleic acid sequences.

Methods for delivering siRNAs, ribozymes and/or antisense oligonucleotides into monocytes are well known in the art and include but are not limited to transfection, electroporation, microinjection, lipofection, calcium phosphate mediated transfection or infection with a viral vector containing the gene sequences, cell fusion, chromosome-mediated gene transfer, microcell-mediated gene transfer, spheroplast fusion, etc. Numerous techniques are known in the art for the introduction of foreign genes into cells and may be used in accordance with the present invention, provided that the necessary developmental and physiological functions of the recipient cells are not disrupted. The technique may provide for the stable transfer of the gene to the cell, so that the gene is expressible by the cell, heritable and expressible by its cell progeny. Usually, the method of transfer includes the transfer of a selectable marker to the cells. The cells are then placed under selection to isolate those cells that have taken up and are expressing the transferred gene. Those cells are then delivered to a subject. A variation of the technique may provide for transient transfer of oligonucleotides or oligonucleotide coding genes to monocytes to enable temporary expansion of monocytes ex vivo or in vivo without permanent genetic modification.

In a further embodiment expression of MafB and C-Maf may be inhibited by compounds acting on promoter activity, RNA processing or protein stability.

In another embodiment, inhibition of the activity activity of MafB and c-Maf may be achieved by using mutated MafB and c-Maf polypeptides which compete with the wild-type MafB and c-Maf.

This technique is generally referred to as the technique of "dominant negative mutants". A dominant negative mutant is a polypeptide or a nucleic acid coding region sequence which has been changed with regard to at least one position in the sequence, relative to the corresponding wild type native version at a position which changes an amino acid residue position at an active site required for biological activity of the native peptide.

For example, a dominant negative mutant may consist of a truncated MafB or c-Maf molecule devoid of N-terminal effector domains that may act as a competitive inhibitor of MafB or c-Maf for DNA binding and transactivation (Kelly et al. 2000). The efficiency of c-Maf/MafB repression may be further improved by fusion to repressor domains that increase inhibitory function.

The methods of the invention are accomplished by exposing monocytes, macrophages or dendritic cells to a dominant negative mutant in vitro. Exposure may be mediated by transfecting the cell with a polynucleotide encoding the dominant negative mutant polypeptide and expressing said dominant negative mutant encoded by the polynucleotide so that MafB and/or c-Maf activity is inhibited. Methods for transfecting such polynucleotides may consist in those above described.

Exposure may also be mediated by exposing monocytes and/or macrophages and/or dendritic cells to a dominant negative mutant polypeptide directly, for instance by contacting the cell with said peptide preferably coupled to an internalization moiety. Suitable internalization moieties are known in the art, and for instance may be selected from the group consisting of a peptide internalization sequence derived from proteins such as TAT polypeptide of HIV or Antennapedia or other homeoproteins. Alternatively transfer may be mediated by a liposome, and an antibody or an antibody fragment or ligand that binds to a surface receptor on the target cell.

As an alternative, inhibitors of activity may consist in molecules which are inhibitors of enzymatic posttranslational modification that regulate activity such as phosphorylation, acetylation, methylation, ribosylation, ubiquitination, small ubiqutin like molecule modification (SUMOylation, neddylation, etc.) or molecules that alter conformation or interaction with co-activators or co-repressors, As a further alternative, inhibitors of activity may consist in inhibitors of DNA binding, dimerization or co-factor interaction.

Inhibitors of activity may include macromolecules or small organic molecules. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The method as above described comprises a step of expanding the cells in the presence of at least one cytokine.

Cytokines may include but are not limited to SCF, Flt3 ligand, Il-3 and M-CSF. Such cytokines are commercially available.

In a preferred embodiment, cells are maintained and expanded in the presence of M-CSF. Macrophage colony stimulating factor (M-CSF) is a member of the family of proteins referred to as colony stimulating factors (CSFs). M-CSF is a secreted or a cell surface glycoprotein comprised of two subunits that are joined by a disulfide bond with a total molecular mass varying from 40 to 90 kD (Stanley E R et al. 1997). Several secreted and membrane bound variants are known (Pixley and Stanley, 2004). M-CSF is produced by macrophages, monocytes, osteoblasts, endothelial cells and human joint tissue cells, such as chondrocytes and synovial fibroblasts, in response to proteins such as interleukin-1 or tumor necrosis factor-alpha. M-CSF stimulates the formation of macrophage colonies from pluripotent hematopoietic progenitor stem cells (Stanley E. R., et al., Mol. Reproid. Dev., 46:4-10 (1997)). M-CSF is an important regulator of the function, activation, and survival of monocytes/macrophages. Recombinant murine or human M-CSF are commercially available from R&D SYSTEMS, ABCYS, PREPO-TECH, SIGMA or STEM CELL TECHNOLOGIES.

The concentration of M-CSF in the culture medium can amount from 1 ng/ml to 100 ng/ml, preferably 5 to 50 ng/l and in a particularly preferred manner 10 ng/l.

Alternatively it is possible to grow the cells in culture medium containing 20% supernatant of L929 fibroblasts as a source of murine M-CSF (available from ATCC: CCL-1). As a source of human M-CSF the KPB-M15 cell line can be used instead.

The monocytes, macrophages or dendritic cells so obtained may be cultured during a least one month. preferably at least 4, 5, 6, 7, 8, or 12 months.

MafB/c-Maf Deficient Cells

The method of the invention leads to the generation of monocytes, macrophages or dendritic cells of great interest in the therapeutic field.

An object of the invention is thus a monocyte, macrophage or dendritic cell obtainable by the method as above described. Preferably the monocyte, macrophage or dendritic cell is in isolated form.

Another object of the invention is a monocyte, macrophage or dendritic cell, which does not express MafB and c-Maf. Preferably the monocyte, macrophage or dendritic cell lacks the MafB and c-Maf genes.

The monocyte, macrophage, or dendritic cell may be of any species. It is preferably from a murine origin, or from a human origin.

When the cell is a dendritic cell, it may be useful to sensitize the cell to antigens. For that purpose, one may contact the dendritic cells with the antigenic molecule of interest or antigenic peptides for about 30 minutes to about 5 hours ("peptide or antigen pulsing"). One can also contact dendritic cells with cells or membranes of cells expressing antigens or antigenic peptides, with liposomes containing antigens or antigenic peptides or with RNAs coding for antigens or antigenic.

A particular subject of the invention is thus a dendritic cell as defined above, i.e. MafB and c-Maf deficient, which is further loaded with an antigenic molecule.

The antigenic molecule may be any molecule against which an immune response is sought. Examples of antigen molecules comprise for instance viral proteins or peptides, bacterial proteins or peptides, or tumor antigens, such as MART-1, MAGE, BAGE, PSA, p53, Rb, Ras, etc.

Mouse Monocytes

Another object of the invention relates to a method for generating murine monocytes wherein said method comprises the steps consisting of:
i) isolating monocytes derived from a mouse deficient for MafB and c-Maf factors and
ii) culturing said cells in the presence of M-CSF Mouse embryos deficient for MafB and c-Maf may be obtained through the crossing of MafB deficient mice with c-Maf deficient mice. Generation of MafB deficient mice has been previously described (Blanchi B. et al., 2003). The generation of c-Maf deficient mice has also been described (Kim J L. et al. 1999), Mice with a MafB and c-Maf deficient hematopoietic system may be obtained by reconstituting irradiated mice with MafB and c-Maf deficient fetal liver cells. Such a method is described in the below example.

Another object of the invention relates to a MafB/Cmaf deficient mutine monocyte obtainable by tissue specific deletion of MafB and c-Maf using a loxP/Cre recombinase system.

Another object of the invention relates to a MafB/c-Maf deficient murine monocyte obtainable by the method as above described.

MafB/c-Maf deficient murine macrophages, or dendritic cells may be obtained through the differentiation techniques as above described.

Cell Therapy

According to the present invention, monocytes, macrophages and dendritics cells can be easily and effectively generated in vitro. The ability to obtain a large number of in vitro expanded monocytes, macrophages and dendritic cells opens new opportunities for the therapeutic field.

The invention thus provides a pharmaceutical composition comprising a monocyte, macrophage or dendritic cell as defined above, in combination with a pharmaceutically acceptable carrier.

The invention further provides a pharmaceutical composition which comprises the dendritic cell as defined above, loaded with an antigenic molecule, for use as a vaccine.

The mononuclear phagocyte system (monocyte and macrophages) represents a distributed organ responsible for homeostasis within the host. Said system is involved in every disease process in which there is persistent tissue injury or metabolic disturbance. Macrophages and monocytes mediate acute as well as chronic inflammation, and promote repair through removal of dead cells and fibrin by phagocytosis and fibrinolysis, induce blood vessel ingrowth (angiogenesis) and modulate fibroblast invasion and production of extracellular matrix. They produce mediators that mobilize systemic responses of the host including fever, release and catabolize stress and other hormones, increase metabolic activity of other cells, and influence blood flow to tissues and capillary permeability. The macrophages themselves display considerable heterogeneity in their functions, often expressing activators as well as inhibitors of a property, e.g. proteolytic activity, or pro- and anti-inflammatory cytokine production, depending on the evolution of a particular host response.

It is therefore described a method for treating a subject affected with a disease resulting from a deficiency in the monocyte compartment, which method comprises administering said subject with monocytes, macrophages or dendritic cells, in which MafB and c-Maf expression or activity is inhibited, preferably with MafB and c-Mat deficient monocytes, macrophages or dendritic cells.

A further object of the invention is the use of a monocyte, macrophage or dendritic cell as defined above for the manufacture of a medicament intended for the treatment of a disease selected from the group consisting of a cancer, acute or acquired immuno-deficiencies, chronic or acute injury, wounds, degenerative diseases, autoimmune diseases, chronic inflammatory diseases, atherosclerosis, poly- and osteo-arthritis, osteoporosis, infectious diseases (e.g. infections by virus, or bacteria), and metabolic diseases.

Immunodeficiencies include acquired or genetic in origin, or as a result of radiotherapy/chemotherapy. AIDS is particularly contemplated. Also, the invention offers the possibility for the development of antigen-specific cancer immunotherapies.

Macrophages according to the invention may be useful for the treatment of HIV infections. Dysfunction of neutrophils (polymorphonuclear leukocytes [PMNL]) and macrophagic cells occurs indeed as a consequence of human immunodeficiency virus type 1 (HIV-1) infection. Macrophages contribute to the resolution of early inflammation ingesting PMNL apoptotic bodies. A recent study suggests that impaired macrophage phagocytosis of PMNL apoptotic bodies may contribute to the persistence of the inflammatory state in HIV-infected subjects, especially during opportunistic infections that are often favored by defective phagocytic activity (Torre D et al. 2002). Therefore, methods for generating macrophages as above described may be useful for the treatment of subjects infected with HIV.

Patients on chemotherapy with anticancer agents such as cyclophosphamide (CP) experience a strong reduction in the size of tissue macrophage populations that accompanies blood leukopenia. These patients are thus especially susceptible to opportunistic infections, including gram-negative bacterial pneumonia. Such opportunistic infections are a common cause of death in cancer patients who are undergoing chemotherapy (Santosuosso M, et al. 2002). Therefore, methods for generating macrophages as above described may be useful for the treatment of subjects who have undergone a chemotherapy.

Macrophages may inhibit precursor cells apoptosis in a cell to cell contact and may serve as stromal support for efficient cellular engraftment for tissue repair (see for example document WO2005014016). In particular macrophages could inhibit myogenic precursor cells apoptosis. Therefore methods for generating macrophages as above described may be useful for the treatment of lesions such as bone or muscular lesion, possibly resulting from a disease or an injury. It can be for example a bone fracture, or a torn muscle. In a more particular embodiment of the invention, said lesion is a cardiac lesion or injury. In particular, it can be for example myocardial infarction, heart insufficiency, coronary thrombosis, dilated cardiomyopathy or any cardiomyocyte dysfunction subsequent to, or resulting from, any genetic defect. Therefore, methods for generating macrophages as above described may be useful for the treatment of acute cardiac insufficiencies with bad prognostic despite progress in treatments, such as infiltrative cardiomyopathy, or cardiomyopathy due to anthracyclin toxicity or cardiomyopathy secondary to HIV infection.

Methods for generating macrophages as above described may be also useful for the treatment of spinal cord injury. A therapy for complete spinal cord injury (SCI) may be indeed consisting in autologous grafts of macrophages that have been educated to a wound-healing phenotype by co-incubation with skin tissue (Schwartz M et al. 2006).

Macrophages are essential for wound healing and thus methods for generating macrophages as above described may be useful for enhancing wound healing and/or repairing tissue damage. The wound healing process has indeed 3 phases. During the inflammatory phase, numerous enzymes and cytokines are secreted by the macrophage. These include collagenases, which clear the wound of debris, interleukins and tumor necrosis factor (TNF), which stimulate fibroblasts (to produce collagen) and promote angiogenesis; and transforming growth factor α (TGFα), which in healing skin wounds stimulates keratinocytes. This step marks the transition into the process of tissue reconstruction, ie, the proliferative phase.

Macrophages play a major role in chronic inflammatory and auto-immune disease and usually are activated or hyperactivated in a specific way under these conditions. Monocytes may be amplified by the described method to be genetically modified, pharmacologically treated or alternatively activated or stimulated by bio-active molecules such as cytokines or growth factors to present a desirable phenotype before introduction into a subject to compete with and supplant macrophages with undesired activity.

Cancer is the second leading cause of death in most developed countries accounting for about 150,000 and 550,000 deaths each year in France and USA, respectively. Despite the fact that more than half of all cancer cases can be cured, the average cancer patient, not curable by surgery or radiotherapy, still has a less than 10% chance of being cured by any other treatment (A. Grillo-Lopez, 2003). It has long been hypothesized and it is now recognized that the immune system plays a role in cancer surveillance and in the prevention of tumors.

Macrophages are a major component of the leukocyte infiltrate of tumors and have been shown to have both positive and negative effects on tumor formation and progression, where the final outcome depends to a large degree on micro-environment dependent polarization of tumor associated macrophages (TAM). Ex vivo amplified and modified macrophages could therefore be therapeutically useful to bring macrophages of desired polarization profile or that carry therapeutic gene constructs or reagents to the tumor site (Single et al., 2002) (Mantovani et al., 2002). Moreover dendritic cells (DC) prime naive T cells to become effector cells able to provide long-term protection against tumor recurrence. Cell therapy based on these two types of cells appears therefore as a promising tool to treat cancer patients. Therefore methods for generating macrophages and/or dendritic cells as above described may be useful, for treating cancer diseases.

Dendritic cells may be induced to mature (maturing DC) through a short treatment with a bacterial extract and interferon-gamma. Furthermore, therapeutic vaccination against tumors has been shown to provide long-term protection in animal models. Tumor (or tumor cell line) lysates constitute an attractive source of multiple tumor antigens to trigger both CD8 and CD4 T cell responses. Therefore pulsing dendritic cells with such tumor antigens, represents a tool for the treatment of cancer.

Therefore methods of the invention may be useful for preparing pharmaceutical compositions comprising macrophages and/or dendritic cells for treating cancer. Cancer include carcinomas of breast, colon, rectum, lung, oropharynx, hypopharynx, esophagus, stomach, pancreas, liver, gallbladder and bile ducts, small intestine, kidney, bladder, urothelium, female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, such as astrocytomas, gliomas, glioblastomas, retinoblastomas, neuromas, neuroblastomas, Schwannomas, and meningiomas, and tumors arising from hematopoietic malignancies such as leukemias as well both Hodgkin's and non-Hodgkin's lymphomas.

In treating cancer, for example, dendritic cells can be pulsed with tumor antigens and administered to a patient to treat, e.g., established tumors, or to prevent tumor formation, as discussed above.

In another embodiment a dendritic cell of the invention may be fused to a cancer cell and therefore can be administered to the patient, wherein the fused dendritic cell will, in its role as an antigen-presenting cell, present the antigen to the immune system. Dendritic cells can be fused with other cells, e.g., cancer cells, by any method known in the art. For example, methods for fusing dendritic cells with cancer cells, as well as methods for administering them to animals have been described in Gong et al. (Nat. Med. 3 (5): 558-561 (1997)) and Guo et al. (Science 263: 518-520 (1994)). The cancer cell can be any type of cancer cell to be targeted in a patient, e.g., cancer cells of the breast, liver, skin, mouth, pancreas, prostate, urinary tract, e.g., bladder, uterus, ovary, brain, lymph nodes, respiratory tract, e.g., larynx, esophagus, and lung, gastrointestinal tract, e.g., stomach, large and small intestine, colon, or rectum, bone, blood, thyroid, and testes, or any cancer cell line known in the art to be suitable for fusing to other cells e.g., dendritic cells.

Similar vaccination protocols may be applied to infectious diseases by loading the dendritic cells with pathogen (viral, bacterial or parasite) antigen.

In a preferred embodiment, monocyes, macrophages, or dendritic cells are obtained directly from the subject to whom they are administered. In that case the transplantation is autologous. But in another embodiment the transplantation can also be non-autologous. For non-autologous transplantation, the recipient is preferably given an immunosuppressive drug to reduce the risk of rejection of the transplanted cell. Methods of administering cells according to the invention include but are not limited to intradermal, intramuscular, intraperitoneal, intravenous, subcutaneous, intranasal, and epidural routes. The cells may be administered by any convenient route, and may be administered together with other biologically active agents. The route of administration is preferably intravenous or intradermal. The titer of monocytes and/or macrophages and/or dendritic cells transplanted which will be effective in the treatment of a particular disease or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances.

Pharmaceutical Compositions

The present invention provides pharmaceutical compositions. Such compositions comprise a therapeutically effective amount of a monocyte and/or macrophage and/or dendritic cell produced according to the invention, and a pharmaceutically acceptable carrier or excipient. By a "therapeutically effective amount" of a cell as above described is meant a sufficient amount of said cell to treat a disease or disorder at a reasonable benefit/risk ratio applicable to any medical treatment. It will be understood, however, that the total daily usage of compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific cells employed; and like factors well known in the medical arts Pharmaceutically acceptable carrier or excipient includes but is not limited to saline, buffered saline, dextrose, water, glycerol and combinations thereof. The carrier and composition can be sterile. The formulation should suit the mode of administration. The composition, if desired, can also contain minor amounts of wetting or emulsifying agents, or pH buffering agents. The composition can be a liquid solution, suspension, or emulsion. In a preferred embodiment, the composition is formulated in accordance with routine procedures as a pharmaceutical composition adapted for intravenous administration to human beings. Typically, compositions for intravenous, administration are solutions in sterile isotonic aqueous buffer. Where necessary, the composition may also include a solubilizing agent and a local anesthetic such as lignocaine to ease pain at the site of the injection.

Methods for Engineering Cells of the Invention

Monocytes, macrophages and dendritic cells of the invention may be further genetically engineered so that said cells express a therapeutic nucleic acid of interest, which encodes a protein of interest.

Suitable gene of interest include growth factors. For instance, cells of the invention can be genetically engineered to produce gene products beneficial upon transplantation of the genetically engineered cells to a subject. Such gene products include, but are not limited to, anti-inflammatory factors, e.g., anti-TNF, anti-IL-6, anti-IL-2 . . . etc. Alternatively, cells of the invention can be genetically engineered to "knock out" the expression of MHC in order to lower the risk of rejection.

Macrophages have been shown to fuse with muscle cells or hepatocytes and can correct a genetic defect in these cells (Camargo et al., 2003) (Camargo et al., 2004) (Willenbring et al., 2004). Cells of the invention may therefore be also engineered to express multiple or single copies of normal or hyperactive variants of genes that are mutated in genetic disorders. Examples include but are not limited to enzyme deficiencies in the liver or dystrophin in Duchenne muscular dystrophy.

Macrophages are a major component of the tumor infiltrate. Suitable genes of interest to be expressed by the cells of the invention may therefore also be genes that carry anti-tumor activity.

Furthermore cells of the invention can be engineered to inhibit expression of genes by siRNA or antisense or siRNA or antisense encoding genes that are stably or transiently introduced into the cells. Targets for inhibition include but are, not limited to inflammatory cytokines, proteases, transcription factors and enzymes affecting inflammatory pathways.

In addition, cells of the invention can be genetically engineered for expressing a growth factor that promotes differentiation and/or proliferation.

Monocytes, macrophages and dendritic cells of the invention may be further engineered so that said cells carry a molecule of interest.

Suitable molecule (or even genes) of interest include protease inhibitors or knockdown of proteases, transcription factors or dominant versions thereof to globally inhibit expression of inflammatory mediators, cytokines, chemokines, proteases or to globally induce anti-inflammatory mediators, cytokines chemokines and protease inhibitors. Genes of interest may encode for cytokines and enzymes that selectively effect M1/M2 polarization of macrophages (II-4, II-10, II-13, TGFβ), or for cytokines inhibiting osteoclast differentiation (such as anti RANKL, OPN), or for growth factors and protease inhibitors stimulating wound healing (such as PDGF, EGF, SLPI), or for anti-microbial peptides.

The delivery of said genes may be performed by any method well known in the art as above described.

Regenerative Medicine

Because of the inadequate supply of donor organs, alternatives to allografts are desperately needed. Cell-replacement therapies may provide a promising alternative to liver, pancreas, or islet cell transplantation. Such therapies may also provide treatment options in organ systems where transplantation is not possible or indicated. It has been recently shown that not only stem or progenitor cells but also committed myelo-monocytic cells, including mature monocytes, macrophages provide a significant potential for targeted and well-tolerated cell therapy aimed at organ regeneration, especially in the liver and pancreas. It has been shown that such mature myelo-monocytic cells of both murine and human origin can significantly contribute to liver and beta-islet pancreatic tissue in different mouse models and perform tissue specific functions in these organs (Camargo, F. D., Green, R., et al, 2003; Willenbring, Bailey et al. 2004; Ruhnke, Ungefroren et al. 2005). Although the mechanism of this is not entirely clear, these observations indicate that the administration of macrophages directly to the damaged organ or systemic transplantation of their proliferative progenitors represents an attractive and little invasive therapeutic strategy. The prospect of a clinical application of this approach, however, is hampered by the difficulty to amplify sufficient numbers of monocytes in culture.

The monocytes, macrophages or dendritic cells obtained by the method of the invention can be used in regenerative medicine, e.g. for administration directly to a damaged organ, or systemic transplantation.

Screening Methods

In certain diseases, it may be desired either to destroy or reduce the number of monocytes, macrophages or dendritic cells, or to target and treat infected monocytes, macrophages or dendritic cells. In such cases, it is desired to develop drugs that target monocytes, macrophages, or dendritic cells.

The method of the invention for generating monocytes, macrophages, or dendritic cells may be useful for screening such drugs.

A general method for screening drugs, which method comprises contacting a monocyte, a macrophage, or dendritic cell as defined above, with a candidate compound, and determining the ability of said compound to bind, and optionally destroy, said cell, to inhibit its replication, or to modify its behaviour. In particular, the candidate compound may change the behaviour of the cell (e.g. its ability to differentiate) in response to a particular stimulus, e.g. a cytokine.

For example, several pathogens are able to subvert the phagocytose process by a range of stratagems utilizing a vacuolar pathway for invasion and survival, even in macrophages. Other examples are known by which organisms evade ingestion (mycoplasma), destroy opsonins enzymatically, inhibit fusion and acidification (mycobacteria) and recruit novel membranes (Legionella) as well as other organelles. *Trypanosoma cruzi* and *Candida albicans* rapidly recruit lysosomes, perhaps to promote their own differentiation. Leishmania multiplies freely within phagolysosomes whereas Listeria monocytogenes disrupts lysosomal membranes and escapes into the cytoplasm, where it initiates actin polymerization for intracellular movement and intercellular spread. Bacteria of the genus *Brucella* are intracellular pathogens capable of survival and replication within macrophages of mammalian hosts. This pathogen uses multiple strategies to circumvent macrophage defense mechanisms and generate an organelle permissive for replication. Finally, the facultative intracellular pathogen *Salmonella enterica* triggers programmed cell death in macrophages.

Therefore the methods for generating macrophages as above described may be useful for screening drugs against pathogens such as *Mycoplasma, Mycobacteria, Legionella, Trypanosoma, Leishmanias, Listeria, Brucella* or *Salmonella*.

The macrophage also contributes to the initial infection, dissemination and persistence of human immunodeficiency virus type 1 (HIV-1) in the body. Known factors that influence infection of macrophages by different HIV strains include CD4 and chemokine coreceptors for viral entry.

Therefore the methods for generating macrophages as above described may be useful for screening drugs against HIV infections.

Methods of the invention may be also useful for screening drugs that inhibit an inflammatory response in macrophages for use against chronic inflammatory and autoimmune disease (such as polyarthritis, Crohns disease or multiple sclerosis) or cancer with a strong contribution of inflammatory tumor associated macrophages.

Methods for generating macrophages as above described may also be useful for screening drugs promoting wound healing or reducing scarring.

Methods for generating macrophages as above described may be useful for screening drugs inhibiting osteoclast differentiation for use in osteoarthritis and osteoporosis.

FIGURES

FIG. 1: 20,000 fetal liver cells from wt (open bars) or MafB/c-Maf double deficient (filled bars) E14.5 embryos were incubated in semisolid medium containing a cytokine mix of recombinant SCF, GM-CSF, IL-3, IL-6, and EPO (A) or 10 ng/ml of recombinant M-CSF (B), GM-CSF (C), G-CSF (D) or Il-3 (E) only. Colonies were scored after 12 days and the average numbers of CFU-M, CFU-E, CFU-GEMM, CFU-GM and CFU-G are indicated. Experiments, were performed in duplicate and error bars indicate standard error of the mean from three individual embryos of each genotype.

FIG. 2: 10,000 fetal liver cells from wt (diamonds) or MafB/c-Maf double deficient (squares) E14.5 embryos were incubated in semisolid medium containing 10 ng/ml of recombinant M-CSF, GM-CSF, or Il-3 as indicated. Colonies were scored every 8 days, washed out from the medium and replated at the same concentration and under the same conditions. Assays were performed in duplicate and two independent, experiments showed equivalent results.

FIG. 3: Fetal liver cells, from wt, MafB deficient, c-Maf deficient or MafB/c-Maf double deficient E14.5 embryos as indicated were differentiated to monocytes/macrophages for 9 days in L-cell conditioned medium as a source of M-CSF, simulated for 24 h with the indicated concentration of recombinant M-CSF and assayed for proliferation by monitoring cells in S-phase after 18 h of BrdU incorporation. The proliferation index as the ratio of proliferation in the stimulated to the non-stimulated cultures is indicated. Error bars indicate standard error of the mean from triplicate samples and two independent experiments showed equivalent results.

Figure 4:
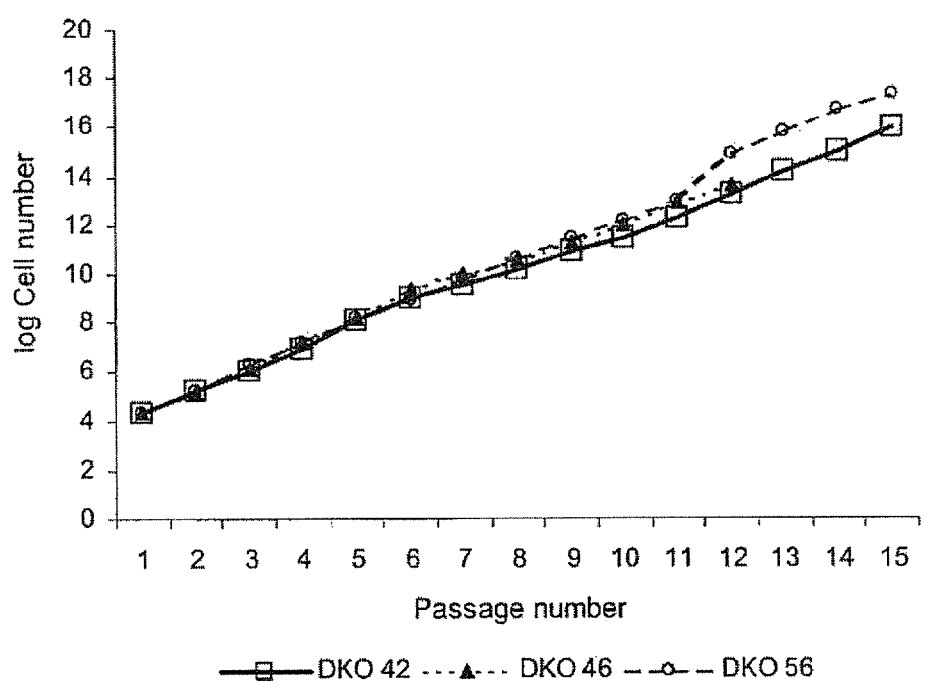

FIG. 4: Three independent monocyte cultures were derived from M-CSF colony assays of MafB/c-Maf double deficient E14.5 fetal liver cells by washing out the cells from the semi-solid medium and incubating them in L-cell conditioned medium as a source of M-CSF. Medium was changed every 4 days and cultures were counted and passaged at confluency. The graph shows the calculated total number of cells derived after the indicated number of passages.

Figure 5:
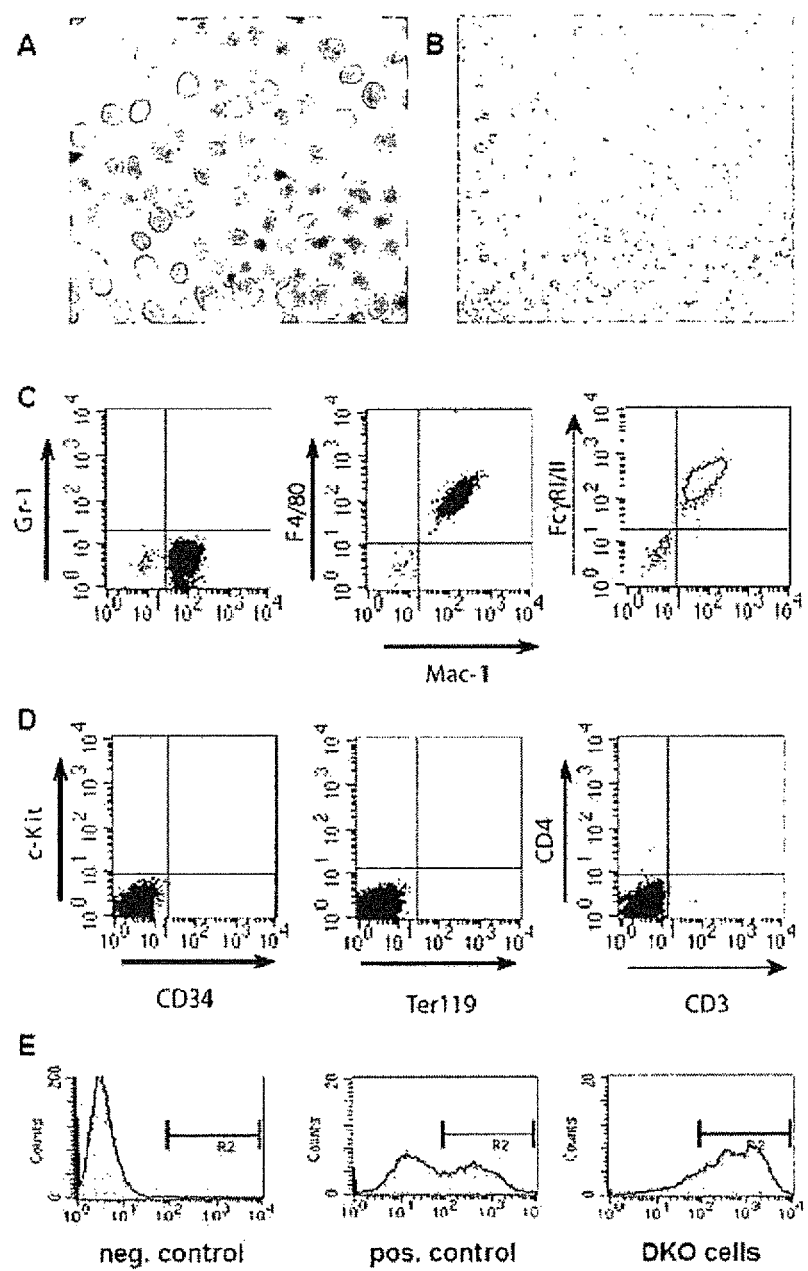

FIG. 5 Phenotypic and functional characterization of MafB/c-Maf double deficient monocyte cultures: A Giemsa staining of a cytospin from MafB/c-Maf double deficient monocyte cultures showing a homogenous monocyte/macrophage morphology. B. Phase contrast photomicrograph of MafB/c-Maf double deficient monocyte cultures C./D. FACS profiles of MafB/c-Maf double deficient monocyte cultures stained for antigens of the myeloid lineage (C) or other lineages (D). Cells were nearly 100% positive for monocyte/macrophage antigens (Mac-1, F4/80 and FcgRII/III) but negative for the granulocytic marker Gr-1, the progenitor markers c-kit and CD34, the erythroid marker Ter119, and the T-lymphoid markers CD3 and CD4. They were also negative for the B-lymphoid marker CD19 (not shown). E. MafB/c-Maf double deficient monocyte cultures (DKO cells) were incubated with PE-coated latex beads and analyzed by FACS for ingested fluorescent beads as a measure of phagocytosis. For comparison phagocytic activity of the RAW 267 macrophage cell line is shown as a positive control. The negative control shows cells not incubated with beads.

Figure 6:
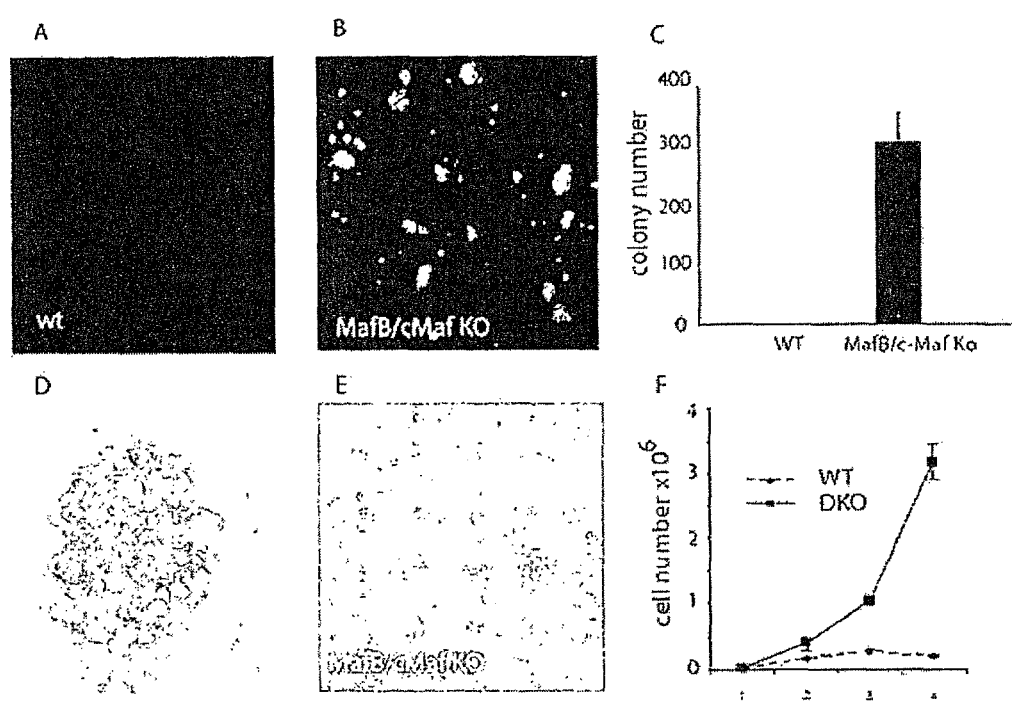

FIG. 6: Derivation of monocyte cultures from MafB/c-Maf deficient blood of aged mice. A.-D. 100,000 white blood cells (WBC) form peripheral blood of 22 months old mice reconstituted either with wt or MafB/c-Maf double deficient fetal liver cells at 2 months of age were incubated in semisolid medium containing 100 ng/ml recombinant M-CSF and analysed for colony formation after 12 days, Photomicrographs of colonies in wt (A) or MafB/c-Maf deficient (B) samples and graph (C) showing the total number of colonies from wt or MafB/c-Maf deficient samples. Error bars indicate standard error of the mean of duplicate samples from two individual mice of each genotype. A magnification of an individual colony in B is shown in panel D. E, F. 100,000 WBC form peripheral blood of wt or MafB/c-Maf deficient reconstituted mice were cultured in L-cell conditioned medium as a source of M-CSF, counted and passaged every 8 days. A phase contrast photomicrograph of a MafB/c-Maf deficient monocytic culture is shown in E and the calculated total number of cells at each indicated passage number is shown in F.

EXAMPLE

Material and Methods

Mice We described previously the generation of MafB deficient mice on a 129Sv-C57BL/6 background and their genotyping by PCR with primers for mafB and gfp, replacing mafB in the knockout allele (Blanchi et al. 2003). The generation of c-Maf deficient mice has also been described (Kim et al. 1999). MafB+/− and c-Maf+/− mice were crossed to obtain MafB;c-Maf+/−;+/− mice, which were intercrossed to obtain MafB;c-Maf−/−;−/− embryos. All experiments were performed in accordance with institutional guidelines using mice maintained under specific pathogen-free conditions.

Fetal Liver cell preparation Embryos were collected aseptically at embryonic day E14.5. A single cell suspension was prepared in primary cell medium (IMDM, 20% FCS, 1% penicillin/streptomycin) from the liver of each embryo and stored at 4° C. until the genotype was confirmed by PCR.

Colony assays: $2\times10^4$ fetal liver cells were seeded in semi-solid medium containing MethoCult M3232 containing a mix of cytokines (SCF, Epo, GM-CSF, II-3, II-6) or MethoCult M3234 (Stem Cell Technologies, Vancouver, Canada) supplemented with 10 murine rM-CSF, 10 ng/rill murine rGM-CSF, 10 ng/ml murine rG-CSF or 10 ng/ml murine rII-3 (Pepro Tech Incorporation) according to manufacturer's instructions. Briefly, 300 ml of cell containing medium was mixed with 300 ml cytokine containing medium, added to 1400 ml of methylcellulose medium and mixed vigorously before plating 900 ml each of this mix in duplicate 35 mm plates. Size and total number of colonies with more than 16 cells were scored in duplicate plates after 4, 6, 9 and 12 days.

Replating assays: $1\times10^4$ fetal liver cells per plate were seeded in semi-solid medium containing methyl cellulose (M3234, Stem Cells Technologies) supplanted with 50 ng/ml murine rM-CSF, murine rGM-CSF or murine rII-3 (allPepro Tech Incorporation). After 8 days colonies were counted and cells were washed repeatedly in medium to remove methyl-cellulose until a single cell suspension was obtained. $1\times10^4$ cells were re-plated under the same conditions and colony formation was scored again after day 8. Re-plating was repeated three times.

Growth of MafB/c-Maf deficient cells in liquid culture: After the 4th plating only MafB/c-Maf deficient cells under M-CSF conditions still gave colonies. These were repeatedly washed in medium to remove methyl-cellulose and taken into liquid culture at $1\times10^4/100$ ml DMEM/10% heat inactivated FCS/1% penicillin/streptomycin and 1% Na-Pyruvate, supplemented with 20% L-cell supernatant as a source of M-CSF. Culture in recombinant murine M-CSF resulted in identical growth characteristics. Cells were subjected to a partial medium change every 4 days and split 1:4 with a complete medium change every 8 days.

L-Cell supernatant production L929 fibroblasts (available from ATCC: CCL-1) were used as source of murine M-CSF conditioned medium. L-Cells were cultured and maintained in L-cells growth medium (DMEM, 10% FCS HI, 1% Na Pyrute, 1% penicillin/streptomycin). For producing supernatant, cells were grown to 70% confluency and medium was changed to L-cells supernatant medium (IMDM, 2% FCS HI, 1% Na Pyruvate, and 1% Penicillin/Streptomycin). Supernatant was collected after 5 days and further medium was added for another 5 days. After collecting the second supernatant both were pooled and filtered through 0.22 mm filter and stored in aliquots at −20° C.

FACS Analysis: For antibody staining cells were resuspended in filtered FACS medium (02% FCS and if necessary FcgII/III blocking antibody in PBS) at a concentration of $1\times10^6$ to $1\times10^7$ cells/ml followed by incubation at 4° C. for 30 min with properly diluted, fluorochrome monoclonal antibodies. Directly flurochrome labelled antibodies against mouse antigens were purchased from BD or from eBiosciences. After washing twice with PBS cells were analysed on a FACSCalibur or FACS Canto machine (Becton-Dickinson, San Jose, Calif.). Data were and analysed with Cell Quest® (Becton-Dickinson) or Flowjo® software.

Phagocytosis assay: Fluorescent beads (Molecular Probes, 1 µM, F-8851) were washed once in sterile PBS, resuspended in DMEM/10% FOS and sonicated for 10 intervals at 10 seconds each. 25 µl of bead solution was incubated macrophages in 24-well plates for 2 hours. Cells were then extensively washed with PBS, fixed with 1% PFA and analyzed by flow cytometry on a FACSCalibur (Beckton Dickinson).

Bone marrow reconstituted mice: For reconstitution experiments a single cell suspension from fetal liver cells of the same genotypes (MafB;c-Maf−/−;−/− or WT) were pooled, filtered through 100 µm gaze, washed once with either 1×HBSS or PBS and re-suspended in PBS or HBSS for injection. $1\times10^6$ FL cells in 200 µl of PBS/HBSS were injected into the tail vein of lethally irradiated (900-1000 rad) age- and sex-matched Ly5.1 recipient mice. Irradiation was done at least 4 hours before cell transfer and mice were kept on antibiotics in the drinking water for 4 weeks post-transplantation.

Proliferation assay: Fetal liver cells were differentiated for 9 days in M-CSF containing medium, washed in PBS and plated in a 96 well flat-bottom plate at 20,000 cells/well in 200 μl of medium containing the indicated concentrations of recombinant M-CSF. After 36 h BrdU was added at a final concentration of 10 nM and 18 hours later cells were fixed and labeled with anti BrdU-antibody following the protocol of a cell proliferation ELISA BrdU colorimetric kit (Roche cat #1 647 229). Briefly, wells were washed 5× with washing solution and incubated with 100 μl detection reagent. After 20 minutes the ELISA reaction was stopped by adding 25 μl of 1M H2SO4 and the colour product was measured in a spectrophotometer at 450 nm.

Results

MafB, c-Maf double deficient fetal liver cells have increased monocytic colony forming potential: Since MafB deficiency is neonatally lethal, we analyzed the effect of MafB/C-Maf double deficiency on hematopoiesis in the E14.5 fetal liver. FACS staining for lineage specific surface markers revealed no abnormalities of lineage distribution in MafB/c-Maf deficient E14, 5 fetal liver. To quantify the number of cells that could proliferative in response to specific cytokines. MafB/c-Maf deficient or wild type (WT) control cells from E14, 5 embryos were cultured in methyl cellulose medium either with a mix of cytokines (Il-3, Il-6, GM-CSF, SCF and Epo; FIG. 1A) or individual myeloid cytokines (M-CSF, GM-CSF, G-CSF or Il-3, FIG. 1B-E) o. Monocytic colonies (CFU-M) were significantly increased for MafB/c-Maf deficient compared to WT foetal liver cells under all conditions that support monocytic growth, (M-CSF, GM-CSF, IL-3 and mixed conditions), whereas other types of colonies remained in the normal range. Furthermore such an increase in monocytic colonies was not seen in individual MafB or c-Maf deficient foetal liver cells (not shown). This indicated that the combined loss of MafB and c-Maf resulted in an increased number of cells giving rise to monocytic colonies in response to myeloid cytokines.

MafB, c-Maf double deficient CFU-M monocytic cells have enhanced self renewal capacity in M-CSF: To further analyze, whether MafB/c-Maf deficient monocytic cells maintained self renewal potential, we tested the serial replating ability of cells from MafB/c-Maf deficient CFU-M colonies. In such assays colonies were washed out from methocell, dissociated and replated under the same cytokine conditions in fresh methocell cultures.

As shown in FIG. 2 under GM-CSF and Il-3 conditions colonies could be replated both from wt and MafB/c-Maf deficient assays for 3 times but no colonies formed after the $4^{th}$ re-plating. By contrast dramatic differences between WT and MafB/c-Maf KO cells were observed under M-CSF conditions, Whereas WT colonies already disappeared after the second re-plating. MafB/c-Maf deficient cells were forming continuously increasing numbers of colonies in M-CSF up to the $4^{th}$ re-plating, This indicated that MafB/c-Maf deficient foetal liver derived monocytic cells had the ability to specifically self renew and expand in M-CSF.

MafB/c-Maf deficient monocytes show increased proliferation in response to M-CSF: To test whether this increased self renewal potential was due to increased M-CSF dependent proliferation of MafB/c-Maf deficient monocytes we differentiated fetal liver cells of wt, MafB deficient, c-Maf deficient or MafB/c-Maf deficient E14, 5 embryos into monocytes for 9 days and then stimulated these cells with different concentrations of M-CSF for 36 hours. We monitored their rate of DNA synthesis in response to M-CSF and established their proliferation index by comparing the rate of BrdU incorporation after 18 h in stimulated and unstimulated cells. As shown in FIG. 3 wt, MafB deficient or c-Mat deficient monocytes showed nearly no proliferative response to M-CSF. By contrast MafB/c-Maf deficient monocytes showed a dramatic increase of proliferation in response to M-CSF. This indicated that the observed continued expansion MafB/c-Maf deficient monocytes is due to a strongly increased ability to proliferate in response to M-CSF.

MafB/c-Maf deficient monocytes can be maintained in M-CSF culture for several months and expanded by more than $10^{10}$ fold: To further test how long this enhanced self renewal and M-CSF dependent proliferation capacity of MafB/c-Maf deficient monocytes could be maintained, CFU-M monocytic colonies were taken into liquid culture and cultured in the presence of M-CSF containing medium. Under these conditions the cells continued to proliferate and expand in culture. Four cell populations were independently derived from different embryos and replating assays and could be maintained in M-CSF containing culture for at least 15 passages or 4 months without any sign of slowed growth or crisis. Two populations went into crisis at passage 16 but the other two did not show any sign of crisis up to passage 24 or 6.5 months and one of them has been kept continuously in culture for 18 months without crisis or slowed growth. The growth curves up to passage 15 of three of these populations (named DKO 42, 46 and 56) are shown in FIG. 4 Cells frozen at each passage could be easily taken into culture again. The derived populations could also be cloned and at least 6 independent lines derived from individual cells of early passage populations have been established.

The total number of cells obtainable without crisis in long term culture was calculated to represent an amplification factor of at least $10^{10}$. To illustrate this enormous amplification factor, the monocytes present in a typically volume of a routine blood analysis (about 5 ml) would theoretically be sufficient to generate the total monocytes of 10 Million people, if similarly amplified.

c-Maf/MafB deficient monocytic cells in M-CSF cultures have a normal monocyte/macrophage phenotype: c-Maf/MafB deficient cells that were continuously cultured in the presence of M-CSF for extended periods of time maintained a monocyte/macrophage phenotype. As shown in FIG. 5A c-Maf/MafB deficient cells showed a typical macrophage morphology in Giemsa/May-Gruenwaid staining. Their appearance in culture under phase contrast was less flattened than typical macrophage cultures, which is likely an indication of their continued proliferation (FIG. 5A). FACS analysis also showed that the total population of c-Maf/MafB deficient cells expressed the typical monocyte/macrophage markers F4/80, Mac-1 (C011b), M-CSFR (CD115) and FcgRII/III (CD16/CD32) but none of selected T-Cell (CD3, CD4, CD8), B-cell (CD19), erythroid, (Ter-119), granulocytic (Gr-1) markers (FIG. 5C,D). In cultures containing low amounts of M-CSF but not high amounts of M-CSF, CD11c was observed to be upregulated, suggesting that these cells have the potential for DC differentiation, which can be suppressed by the continuous presence of M-CSF. Furthermore c-Maf/MafB deficient cells exhibited typical monocyte/macrophage function, as they were able to quantitatively phagocytose large amounts fluorescent latex beads to a degree equal or higher than wt primary macrophages or macrophage cell lines (FIG. 5E).

Together these observations indicated that despite their continued proliferation in culture all cells maintained a mature phenotype of fully differentiated and functional monocytes/macrophages.

c-Maf/MafB deficient monocytes and macrophages do not develop malignancies in vivo: Increased replating efficiency in vitro is also observed for malignant transformed cells that have leucemic potential in vivo. To control for this possibility we reconstituted lethally irradiated recipient mice with c-Maf/MafB deficient fetal liver cells and observed the reconstituted mice for extended periods of time to analyse whether myeloid leukaemia or myelo-proliferative disorders would develop. So far 8 mice were reconstituted at 6-8 weeks of age and analysed at 8, 11, 14 and 22 months of age, the latter of which is close to the maximal life span of a mouse. During the whole observation period the mice appeared normal and showed no sign of discomfort. Regular blood analysis up to 22 months showed normal white blood cell counts and morphology without indication of blasts or abnormal cells. By FACS analysis monocytes had a normal CD115+, CD11b+, F4/80+, phenotype and no increased numbers of cells expressing immature or progenitor surface markers were detected. Upon sacrifice, dissection also did not reveal any macroscopic signs of leukemia, the spleen presented a normal size and healthy appearance. FACS analysis and histological staining of cytospins from blood, bone marrow, spleen and peritoneal exudate did not reveale any indication of leukaemia or myelo-proliferative disease. No increased numbers of cells with a progenitor surface marker profile (CMP,GMP) or cells with blast or immature morphology were observed in the bone marrow. This indicates that c-Maf/MafB deficient monocytes and monocyte derived cells can contribute normally and long term to the hematopoietic system without causing hematologic pathologies.

c-Maf/MafB deficient monocytes from aged mice can be expanded in M-CSF culture: We wanted to analyze whether c-Maf/MafB deficient monocyte/macrophages with expanded self-renewal capacity could not only be derived from embryonic cells but also from terminally differentiated cells of adult or even aged animals. Therefore we tested whether monocytes from mice reconstituted with a MafB/c-Maf deficient hematopoietic system could be expanded in M-CSF culture and give rise to colonies in M-CSF containing methocell medium. As shown in FIG. 6, monocytes from wt reconstituted mice could not give rise to colonies in M-CSF methocell culture, as was expected. By contrast, c-Maf/MafB deficient white blood cells gave rise to CFU-M monocytic colonies and could be expanded in M-CSF culture. Together this demonstrated that the observed phenotype is not specific to embryonic cells but that MafB/c-Maf deficiency confers extended self-renewal capacity to terminally differentiated monocytes from adult aged mice.

c-Maf/MafB deficient monocyte/macrophage expanded in culture home to peripheral tissues after intravenous injection: To test whether in M-CSF culture expanded c-Maf/MafB cells would emigrate from the circulation into peripheral tissues like normal monocytes, we reinjected $1\times10^6$ Ly5.2+ c-Maf/MafB deficient monocyte/macrophages intravenously into Ly5.1+ hosts and analysed their presence in the circulation and in peripheral tissues after 4, 24 and 4B hours. We observed that CD11b+ donor cells were detectable in the peritoneum from 4 hours on and in the spleen from 24 h on. This indicated that in culture expanded c-Maf/MafB cells could contribute to monocyte derived cell populations in vivo.

REFERENCES

Akira 5, Kishimoto T. Role of interleukin-6 in macrophage function. Curr Opin Hematol. 1996 January; 3(1):87-93.

Alderson M R, Armitage R J, Tough T W, Strockbine L, Fanslow W C, Spriggs M K. CD40 expression by human monocytes: regulation by cytokines and activation of monocytes by the ligand for CD40. J Exp Med. 1993; 178:669-674

Ardavin, C., Martinez del Hoyo, G., Martin, P., Anjuere, F., Arias, C. F., Mann, A. R., Ruiz, S., Parrillas, V., and Hernandez, H. (2001). Origin and differentiation of dendritic cells. Trends Immunol 22, 691-700.

Banchereau J, Steinman R M. Dendritic cells and the control of immunity. Nature. 1998; 392:245-252

Becker, S., Warren, M. K. and Haskill, S. (1987) Colony-stimulating factor-induced monocyte survival and differentiation into macrophages in serum-free cultures. J Immunol, 139, 3703-3709.

Bingle, L., Brown, N. J., and Lewis, C. E. (2002). The role of tumour-associated macrophages in tumour progression: implications for new anticancer therapies. J Pathol 196, 254-265.

Blanchi B, Kelly L M, Viemari J C, Lafon I, Burnet H, Bevengut M, Tillmanns S, Daniel L, Graf T, Hilarre G, Sieweke M H. MafB deficiency causes defective respiratory rhythmogenesis and fatal central apnea at birth. Nat Neurosci. 2003 October; 6(10):1091-100.

Bloom E T B J, Kawakami K. Monocyte-mediated augmentation of human natural killer cell activity: Conditions, monocyte and effector cell characteristics. J Imnnunol. 1986; 137:172

Blusse van Oud Alblas A, van der Linden-Schrever B, van Furth R. Origin and kinetics of pulmonary macrophages during an inflammatory reaction induced by intravenous administration of heat-killed bacillus Calmette-Guerin. J Exp Med. 1981; 154:235-252

Boyle W J, Simonet W S, Lacey D L. Osteoclast differentiation and activation. Nature. 2003 May 15; 423(6937):337-42

Brandslund I, Rasmussen J M, Fisker D, Svehag S E. Separation of human peripheral blood monocytes on continuous density gradients of polyvinylpyrrolidone-coated silica gel (Percoll). J Immunol Methods. 1982:48(2):199-211.

Brossart P, Grunebach F, Stuhler G, Reichardt V L, Mohle R, Kanz L, Brugger W. Generation of functional human dendritic cells from adherent peripheral blood monocytes by CD40 ligation in the absence of granulocyte-macrophage colony-stimulating factor. Blood. 1998 Dec. 1; 92(11):4238-47

Brummelkamp T R, Bernards R, Agami R. A system for stable expression of short interfering RNAs in mammalian cells. Science. 2002 Apr. 19; 296(5567):550-3. Epub 2002 Mar. 21.

Camargo, F. D., Green, R., Capetanaki, Y., Jackson, K. A. & Goodell, M. A. Single hematopoietic stem cells generate skeletal muscle through myeloid intermediates. Nat Med 9, 1520-7 (2003).

Camargo, F. D., Finegold, M., and Goodell, M. A. (2004). Hematopoietic myelomonocytic cells are the major source of hepatocyte fusion partners. J Clin invest 113, 1266-1270.

Carson W E, Ross M E, Baiocchi R A, Marien M J, Boiani N, Grabstein K. Caligiuri M A. Endogenous production of interleukin 15 by activated human monocytes is critical for optimal production of interferon-gamma by natural killer cells in vitro. J Clin Invest. 1995; 96:2578-2582

Carter P, Bedouelle H, Winter G. Improved oligonucleotide site-directed mutagenesis using M13 vectors. Nucleic Acids Res. 1985 Jun. 25; 13(12):4431-43.

Chang Z L W T, Herberman R B. Immunoregulatory role of in vitro differentiated macrophages on human natural killer (NK)-cell activity. Cell Immunol. 1990; 125:183

Chapuis F, Rosenzwajg M, Yagello M, Ekman M, Biberfeld P, Gluckman J C. Differentiation of human dendritic cells from monocytes in vitro. Eur J Immunol, 1997; 27:431-441.

Chokri M, Freudenberg M, Galanos C, Poindron P, Bartholeyns J. Antitumoral effects of lipopolysaccharides, tumor necrosis factor, interferon and activated macrophages; synergism and tissue distribution. Anticancer Res. 1989 July-August; 9(4):1185-90.

Chomarat P, Banchereau J, Davoust J, Palucka A K. IL-6 switches the differentiation of monocytes from dendritic cells to macrophages. Nat Immunol. 2000 December; 1(6):510-4.

Cooper M A, Bush J E, Fehniger T A, VanDeusen J B, Waite R E, Liu Y, Aguila H L, Caligiuri M A. In vivo evidence for a dependence on interleukin 15 for survival of natural killer cells. Blood. 2002; 100:3633-3638

Cordes S P, Barsh G S. The mouse segmentation gene kr encodes a novel basic domain-leucine zipper transcription factor. Cell. 1994 Dec. 16; 79(6):1025-34.

Crofton R W, Diesselhaff-den Dulk M M, van Furth R. The origin, kinetics, and characteristics of the Kupffer cells in the normal steady state. J Exp Med. 1978; 148:1-17

Dobrovolskaia M A, Vogel S N. Toll receptors, CD14, and macrophage activation and deactivation by LPS. Microbes Infect. 2002; 4:903-914

D'Onofrio C, Paradisi F. In-vitro differentiation of human monocytes into mature macrophages during long-term cultures. Immunobiology. 1983 February; 164(1):13-22.

Eichmann, A., Grapin-Botton, A., Kelly, L., Graf, T., Le Douarin, N. M., and Sieweke, M. (1997). The expression pattern of the mafB/kr gene in birds and mice reveals that the kreisler phenotype does not represent a null mutant. Mech Dev 65, 111-122.

Elbashir S M, Martinez J, Patkaniowska A, Lendeckel W, Tuschl T. Functional anatomy of siRNAs for mediating efficient RNAi in Drosophila melanogaster embryo lysate. EMBO J. 2001 Dec. 3; 20(23):6877-88.

Elias J A, Chien P. Gustilo K M, Schreiber A D. Differential interleukin-1 elaboration by density-defined human monocyte subpopulations. Blood. 1985 August; 66(2):298-301.

Erickson-Miller C L, Brennan J K, Abboud C N. Examination of survival, proliferation and cell surface antigen expression of human monocytes exposed to macrophage colony-stimulating factor (M-CSF). Int J Cell Cloning. 1990 September; 8(5):346-56.

Ferlazzo G, Morandi B, D'Agostino A, Meazza R, Melioli G, Moretta A, Moretta L. The interaction between NK cells and dendritic cells in bacterial infections results in rapid induction of NK cell activation and in the lysis of uninfected dendritic cells. Eur J Immunol. 2003; 33:306-313

Ferlazzo G, Tsang M L, Moretta L, Melioli G, Steinman R M, Munz C. Human dendritic cells activate resting natural killer (NK) cells and are recognized via the NKp30 receptor by activated NK cells. J Exp Med. 2002; 195:343-351

Fernandez N C, Lozier A, Frament C, Ricciardi-Castagnoli P, Bellet D, Suter M, Perricaudet M, Tursz T, Maraskovsky E, Zitvogel L. Dendritic cells directly trigger NK cell functions: cross-talk relevant in innate anti-tumor immune responses in vivo. Nat Med. 1999; 5:405-411.

Fluks A J. Three-step isolation of human blood monocytes using discontinuous density gradients of Percoll., J Immunol Methods. 1981; 41(2);225-33.

Foey A D, Feldmann M, Brennan F M. Route of monocyte differentiation determines their cytokine production profile: CD40 ligation induces interleukin 10 expression. Cytokine. 2000; 12:1496-1505

Fogg D K, Sibon C, Miled C, Jung S, Aucouturier P, Littman D R, Cumano A, Geissmann F. A clonogenic bone marrow progenitor specific for macrophages and dendritic cells. Science. 2006 Jan. 6; 311(5757):83-7. Epub 2005 Dec. 1. Erratum in: Science. 2006 Mar. 3; 311(5765);1242.

Fukao, T., and Koyasu, S. (2000). Expression of functional IL-2 receptors on mature splenic dendritic cells. Eur J Immunol 30, 1453-1457.

Fukao, T., Matsuda, S., and Koyasu, S. (2000). Synergistic effects of IL-4 and IL-18 on IL-12-dependent IFN-gamma production by dendritic cells. J Immunol 164, 64-71.

Gabbianelli M, Pelosi E, Montesoro E, Valtieri M, Luchetti L, Samoggia P. Vitelli L, Barberi T, Testa U, Lyman S, et al. Multi-level effects of flt3 ligand on human hematopoiesis: expansion of putative stem cells and proliferation of granulomonocytic progenitors/monocytic precursors. Blood, 1995; 86:1661-1670

Geissler K, Tricot G, Grimm G, Siostrzonek P, Broxmeyer H. Recombinant human colony stimulating factor-granulocyte/macrophage and -granulocyte, but not macrophage induce the development of a respiratory burst in primary human myeloid leukemic cells in vitro. Blut. 1989 September; 59(3):226-30.

Geissmann, F. (2007). The origin of dendritic cells. Nat Immunol 8, 558-560.

Gerosa F, Baldani-Guerra B, Nisii C, Marchesini V. Cerra G, Trinchieri G. Reciprocal activating interaction between natural killer cells and dendritic cells. J Exp Med. 2002; 195:327-333

Gersuk G, Hiraoka A, Marr K A. Human monocytes differentiate into macrophages under the influence of human KPB-M15 conditioned medium. J Immunol Methods. 2005 April; 299(1-499-106.

Gieseler R, Heise D, Soruri A, Schwartz P, Peters J H. In-vitro differentiation of mature dendritic cells from human blood monocytes. Dev Immunol. 1998; 6(1-2):25-39.

Gordon S, Taylor P R. Monocyte and macrophage heterogeneity. Nat Rev Immunol. 2005 December; 5(12):953-64

Gordon S. Alternative activation of macrophages. Nat Rev Immunol. 2003 January; 3(1):23-35

Goud T J, Schotte C, van Furth R. Identification and characterization of the =noblest in mononuclear phagocyte colonies grown in vitro. J Exp Med. 1975; 142:1180-1199

Grillo-Lopez A J. Cancer therapies crisis in the USA. Expert Rev Anticancer Ther. 2003 October; 3(5):579-82.

Hale T K. Myers C. Maitre R, Kolzau T, Nishizawa M, Braithwaite A W. Maf transcriptionally activates the mouse p53 promoter and causes a p53-dependent cell death. J Biol Chem. 2000 Jun. 16; 275(24):17991-9.

Hannon G J. RNA interference. Nature. 2002 Jul. 11; 418 (6894):244-51. Review.

Hardin J A, Downs J T. Isolation of human monocytes on re-orienting gradients of Percoll. J Immunol Methods. 1981; 40(1):1-6.

Harwood R. Cell separation by gradient centrifugation. Int Rev Cytol. 1974; 38(0):369-403.

Hashimoto 5, Yamada M, Motoyoshi K, Akagawa K S. Enhancement of macrophage colony-stimulating factor-induced growth and differentiation of human monocytes by interleukin-10. Blood. 1997 Jan. 1; 89(1015-21.

Hedge, S. P., Kumar, A., Kurschrier, C., and Shapiro, L. H. (1998). c-Maf interacts with c-Myb to regulate transcription of an early myeloid gene during differentiation. Mol Cell Biol 18, 2729-2737.

Hegde, S. P., Zhao, J., Ashmun, R. A., and Shapiro, L. H. (1999). c-Maf induces monocytic differentiation and apoptosis in bipotent myeloid progenitors. Blood 94, 1578-1589.

Hibbs J B, Jr., Taintor R R, Vavrin Z. Macrophage cytotoxicity: role for L arginine deiminase and imino nitrogen oxidation to nitrite. Science. 1987; 235:473-476

Hsu, H. et al. Tumor necrosis factor receptor family member RANK mediates osteoclast differentiation and activation induced by osteoprotegerin ligand. Proc. Natl Acad. Sci. USA 96, 3540-3545 (1999).

Kataoka K, Node M, Nishizawa M. Mat nuclear oncoprotein recognizes sequences related to an AP-1 site and forms heterodimers with both Fos and Jun. Mol Cell Biol. 1994 January; 14(1):700-12.

Kawauchi S, Takahashi S, Nakajima O, Ogino H, Morita M, Nishizawa M, Yasuda K, Yamamoto M. Regulation of lens fiber cell differentiation by transcription factor c-Maf. J Biol Chem, 1999 Jul. 2; 274(27):19254-60.

Kerppola T K, Curran T. Maf and Nrl can bind to AP-1 sites and form heterodimers with Fos and Jun. Oncogene. 1994 March; 9(3):675-84.

Kim J I, Ho I C, Grusby M J, Glimcher L H. The transcription factor c-Maf controls the production of interleukin-4 but not other Th2 cytokines. Immunity. 1999 June; 10(6):745-51.

Kim, K., Kim, J. H., Lee, J. Jin, H. M., Kook, H., Kim, K. K., Lee, S. Y., and Kim, N. (2006). MafB negatively regulates RANKL-mediated osteoclast differentiation. Blood.

Kishimoto T K, Larson R S, Corbi A L, Dustin M L, Staunton D E, Springer T A. The leukocyte integrins. Adv Immunol. 1989; 46:149-182

Kondo M, Wagers A J, Manz M G, Prohaska S S, Scherer D C, Beilhack G F, Shizuru J A, Weissman I L. Biology of hematopoietic stem cells and progenitors: implications for clinical application. Annu Rev Immunol. 2003; 21; 759-806

Kuijpers T. Leukocyte Membrane Adhesion Proteins LFA-1, CR3 and p150, 95: a Review of Functional and Regulatory Aspects. Res Immunol. 1989; 140:461-486

Kurschner C, Morgan J I. The mat proto-oncogene stimulates transcription from multiple sites in a promoter that directs Purkinje neuron-specific gene expression. Mal Cell Biol. 1995 January; 15(1):246-54.

Loos H, Blok-Schut B, van Doom R, Hoksbergen R, Brutal de la Riviera A, Meerhof L. A method for the recognition and separation of human blood monocytes on density gradients. Blood. 1976 November; 48(5):731-42.

Mantovani, A., Sozzani, S., Locati, M., Allavena, P., and Sica, A. (2002). Macrophage polarization: tumor-associated macrophages as a paradigm for polarized M2 mononuclear phagocytes. Trends Immunol 23, 549-555.

Matsuoka T A, Zhao L, Artner I, Jarrett H W, Friedman D, Means A, Stein R. Members of the large Maf transcription family regulate insulin gene transcription in islet beta cells. Mol Cell Biol. 2003 September; 23(17):6049-62.

Mellman I. Fc Receptor Function in Macrophages and Lymphocytes. In van Furth R ed. Mononuclear Phagocytes. Dordrecht, The Netherlands: Kluwer Academic Publishers; 1992

Metcalf D. The colony stimulating factors: discovery, development, and clinical applications. In: Fortner J G R J ed. Accomplishments in cancer research. Philadelphia: J.B. Lippincott Company; 1990

Miller J S, Oelkers S, Verfaillie C, McGlave P. Role of monocytes in the expansion of human activated natural killer cells. Blood. 1992; 80:2221-2229

Mitani H, Katayama N, Araki H, Ohishi K, Kobayashi K, Suzuki H, Nishii K, Masuya M. Yasukawa K, Minami N, Shiku H. Activity of interleukin 6 in the differentiation of monocytes to macrophages and dendritic cells. Br J Haematol. 2000 May; 109(2):288-95.

Naeim F. Pathology of Bone Marrow. In: Mitchell C W ed (ed second). Baltimore: Williams & Wilkins; 1998

Nathan C F. Secretory products of macrophages. J Clin Invest. 1987; 79:319-326

Nathanson S D, Zamfirescu P L, Drew S I, Wilbur S. Two-step separation of human peripheral blood monocytes on discontinuous density gradients of colloidal silica-polyvinylpyrrolidinone. J Immunol Methods. 1977; 18(3-4):225-34.

Nishizawa M, Kataoka K, Goto N, Fujiwara K T, Kawai S. v-maf, a viral oncogene that encodes a "leucine zipper" motif. Proc Natl Aced Sci USA. 1989 October; 86(20):7711-5.

Palucka K A, Taquet N, Sanchez-Chapuis F, Gluckman J C. Dendritic cells as the terminal stage of monocyte differentiation. J Immunol. 1998 May 1; 160(9):4587-95.

Parry S L, Sebbag M, Feldmann M, Brennan F M. Contact with T cells modulates monocyte IL-10 production: role of T cell membrane TNF-alpha. J Immunol. 1997; 158:3673-3681

Pertoft H, Johnsson A, Warmegard B, Seljelid R. Separation of human monocytes on density gradients of Percoll. J Immunol Methods. 1980; 33(3):221-9.

Piccioli D, Sbrana S, Melandri E, Valiante N M. Contact-dependent stimulation and inhibition of dendritic cells by natural killer cells. J Exp Med. 2002; 195:335-341

Pixley, F. J. and Stanley, E. R. (2004) CSF-1 regulation of the wandering macrophage: complexity in action. Trends Cell Biol, 14, 628-638.

Pober J S, Cotran R S. The role of endothelial cells in inflammation. Transplantation. 1990; 50:537-544

Reis e Sousa C. Dendritic cells as sensors of infection. Immunity. 2001; 14:495-498

Ring B Z, Cordes S P, Overbeek P A, Barsh G S. Regulation of mouse lens fiber cell development and differentiation by the Maf gene, Development, 2000 January; 127(2):307-17.

Ruhnke, M., H. Ungefroren, et al. (2005). "Differentiation of in vitro-modified human peripheral blood monocytes into hepatocyte-like and pancreatic islet-like cells." Gastroenterology 128(7): 1774-1786.

Salahuddin S Z, Markham P D, Gallo R C. Establishment of long-term monocyte suspension cultures from normal human peripheral blood. J Exp Med. 1982 Jun. 1; 155(6): 1842-57.

Sallusto, F., A. Lanzavecchia. 1994. Efficient presentation of soluble antigen by cultured human dendritic cells is maintained by granulocyte/macrophage colony-stimulating factor plus interleukin 4 and downregulated by tumor necrosis factor a. J. Exp, Med. 179:1109-18

Sambrook et al., Molecular Cloning: A Laboratory Manual, 3rd edition, Cold Spring Harbor Press, N.Y., (2001)

Santosuosso M, Divangahi M, Zganiacz A, Xing Z Reduced tissue macrophage population in the lung by anti-cancer agent cyclophosphamide: restoration by local granulocyte macrophage-colony-stimulating factor gene transfer, Blood. 2002 Feb. 15; 99(4):1246-52.

Schwartz M, Yoles E. Immune-based therapy for spinal cord repair: autologous macrophages and beyond. J Neurotrauma. 2006 March-April; 23(3-4):360-70.

Shizuru J A, Negrin R S, Weissman I L. Hematopoietic stem and progenitor cells: clinical and preclinical regeneration of the hematolymphoid system. Annu Rev Med. 2005; 56:509-38

Shu U, Kiriiwa M, Wu C V, Maliszewski C, Vezzio N, Hakimi J, Gately M, Delespesse G. Activated T cells induce interleukin-12 production by monocytes via CD40-CD40 ligand interaction. Eur J Immunol. 1995; 25:1125-1128

Shum D T, Gaisworthy S B. Stimulation of monocyte production by an endogenous mediator induced by a component from Listeria monocytogenes. Immunology, 1982; 46; 343-351

Stanley E R, Berg K L, Einstein D B, Lee P S, Pixley F J, Wang Y, Yeung Y G Biology and action of colony—stimulating factor-1. Mol Reprod Dev. 1997 January; 46(1):4-10.

Stanley, E. R. (1986) Action of the colony-stimulating factor, CSF-1. Ciba Found Symp, 118, 29-41.

Stanley, ER., Chen, D. M. and Lin, H. S. (1978) Induction of macrophage production and proliferation by a purified colony stimulating factor. Nature, 274, 168-170.

Stevenson, H. C., Miller, P., Akiyama, Y., Favilla, T., Beman, J. A., Herberman, R., Stull, H., Thurman, G., Maluish, A. and Oldham, R. (1983) A system for obtaining large numbers of cryopreserved human monocytes purified by leukapheresis and counter-current centrifugation elutriation (CCE). J Immunol Methods, 62, 353-363.

Strobl, H., C. Bello-Fernandez, E. Riedl, W. F. Pickl, O. Majdic, S. D. Lyman, W. Knapp. 1997. flt3 ligand in cooperation with transforming growth factor-b1 potentiates in vitro development of Langerhans-type dendritic cells and allow single-cell dendritic cell cluster formation under serum-free conditions. Blood 90:1425-34

Teitelbaum S L, Ross F P. Genetic regulation of osteoclast development and function. Nat Rev Genet. 2003 August; 4(8):638-49

Tillmanns, S., Otto, C., Jaffrey, E., Duroure, C., Bakri, Y., Vanhille, L., Sarrazin, S., Hay, R. T., and Sieweke, M. H. (2007). SUMO-modification regulates MafB driven macrophage differentiation by enabling Myb dependent transcriptional repression. Mol Cell Biol 27, 5554-5564.

Torre D, Gennero L, Baccino F M, Speranza F, Biondi G, Pugliese A. Impaired macrophage phagocytosis of apoptotic neutrophils in patients with human Immunodeficiency virus type 1 infection. Clin Diagn Lab Immunol. 2002 September; 9(5):983-6.

Trinchieri G. Interleukin-12 and the regulation of innate resistance and adaptive immunity, Nat Rev Immunol. 2003; 3:133-146

Tripp C S, Wolf S F, Unanue E R. Interleukin 12 and tumor necrosis factor alpha are costimulators of interferon gamma production by natural killer cells in severe combined immunodeficiency mice with listeriosis, and interleukin 10 is a physiologic antagonist. Proc Natl Aced Sci USA. 1993; 90:3725-3729

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

van Furth R. Production and Migration of Monocytes and Kinetics of Macrophages. In: van Furth R ed. Mononuclear Phagocytes. Dordrecht, The Netherlands: Kluwer Academic Publishers; 1992 van Waarde D, Hulsing-Hesselink E, Sandkuyl L A, van Furth R. Humoral regulation of monocytopoiesis during the early phase of an inflammatory reaction caused by particulate substances. Blood. 1977; 50:141-154

Vey E, Zhang J H, Dayer J M. IFN-gamma and 1.25(OH) 2D3 induce on THP-1 cells distinct patterns of cell surface antigen expression, cytokine production, and responsiveness to contact with activated T cells. J Immunol. 1992; 149:2040-2046

Wagner D H, Jr., Stout R D, Suttles J. Role of the CD40-CD40 ligand interaction in CD4+ T cell contact-dependent activation of monocyte interleukin-1 synthesis. Eur J Immunol. 1994; 24:3148-3154

Wahl S M, Katona I M, Stadler B M, Wilder R L, Helsel W E, Wahl L M. Isolation of human mononuclear cell subsets by counterfiow centrifugal elutriation (CCE). II. Functional properties of B-lymphocyte-, T-lymphocyte-, and monocyte-enriched fractions. Cell Immunol. 1984 May; 85(2):384-95.

Wang P W, Eisenhart J D, Cordes S P, Barsh G S, Stoffel M, Le Beau M M. Human KRML (MAFB): cDNA cloning, genomic structure, and evaluation as a candidate tumor suppressor gene in myeloid leukemias. Genomics. 1999 Aug. 1; 59(3):275-81.

Willems R, Henckaerts E, Lenjou M, Nijs G, Rodrigus I, Moulijn A C, Slegers H, Bememan Z N, Van Bockstaele D R. Establishment of serum-free pre-colony forming unit assays for differentiation of primitive hematopoietic progenitors: serum induces early macrophage differentiation and inhibits early erythroid differentiation of CD3441-CD38-cells. Ann Hematol. 2001; 80:17-25

Willenbring, H., A. S. Bailey, et al. (2004). "Myelomonocytic cells are sufficient for therapeutic cell fusion in liver." Nature Medicine 10(7): 744-748. Wright S D, Ramos R A, Tobias P S, Ulevitch R J, Mathison J C. CD14, a receptor for complexes of lipopolysaccharide (LPS) and LPS binding protein. Science. 1990; 249:1431-1433.

Wu, L., and Liu, Y. J. (2007). Development of dendritic-cell lineages. Immunity 26, 741-750.

Yang Y, ovoid k Tissue-specific regulation of the mouse alphaA-crystallin gene in lens via recruitment of Pax6 and c-Maf to its promoter. J Mol Biol. 2005 Aug. 19; 351(3):453-69.

Yasuda, H. et al. Osteoclast differentiation factor is a ligand for osteoprotegerin/osteoclastogenesisinhibitory factor and is identical to TRANCE/RANKL. Proc. Natl Acad. Sci. USA 95, 3597-3602 (1998).

Yoshida T, Ohkumo T, Ishibashi S, Yasuda K. The 5'-AT-rich half-site of Maf recognition element: a functional target for bZIP transcription factor Maf. Nucleic Acids Res. 2005 Jun. 21; 33(11):3465-78. Print 2005.

Zhou, L. J., T. F. Tedder. 1996. CD14 blood monocytes can differentiate into functionally mature CD83' dendritic cells. Proc. Natl. Acad. Sci. USA 93:2588-92

Zoller M J, Smith M. Oligonucleotide-directed mutagenesis using M13-derived vectors: an efficient and general procedure for the production of point mutations in any fragment of DNA. Nucleic Acids Res. 1982 Oct. 25; 10(20):6487-500.

The invention claimed is:

1. An ex vivo method for expanding monocytes, macrophages or dendritic cells, which method comprises inhibiting the expression or the activity of MafB and c-Maf in monocytes, macrophages or dendritic cells; and expanding the cells in the presence of at least one cytokine, wherein the at least one cytokine comprises an agonist of M-CSF receptor signaling; and wherein said inhibition of both MafB and c-Maf in said cell renders said cell a self-renewing cell in culture.

2. The method according to claim 1, wherein the expression of MafB and c-Maf is inhibited by using siRNA oligonucleotide, antisense oligonucleotide or ribozymes.

3. The method according to claim 1, wherein the activity of MafB and c-Maf is inhibited by using mutated MafB and c-Maf polypeptides which compete with the wild-type MafB and c-Maf.

4. The method according to claim 1, wherein the cytokine is M-CSF.

5. The method of claim 1, wherein said monocyte, macrophage or dendritic cell is of murine origin.

6. The method of claim 1, wherein said monocyte, macrophage or dendritic cell is of human origin.

7. The method of claim 1 wherein said macrophage is selected from the group consisting of microglia, histiocytes, Hofbauer cells, mesangial cells, Kupffer cells, peritoneal macrophages, alveolar macrophage, epidermal or dermal macrophages, marginal zone macrophages, metallophilic macrophages, Red pulp macrophages, white pulp macrophages and osteoclasts.

8. The method of claim 1, wherein said dendritic cell according to is further loaded with an antigenic molecule.

* * * * *